(12) United States Patent
Shojaei et al.

(10) Patent No.: US 12,390,469 B2
(45) Date of Patent: Aug. 19, 2025

(54) SHP2 INHIBITOR MONOTHERAPY AND USES THEREOF

(71) Applicant: HUYABIO International, LLC, San Diego, CA (US)

(72) Inventors: Farbod Shojaei, San Diego, CA (US); Jill M. Ricono, Encinitas, CA (US); Robert Goodenow, San Clemente, CA (US); Mireille Gillings, San Diego, CA (US)

(73) Assignee: HUYABIO International, LLC, San Diego, CA (US)

( * ) Notice: Subject to any disclaimer, the term of this patent is extended or adjusted under 35 U.S.C. 154(b) by 0 days.

(21) Appl. No.: 17/736,908

(22) Filed: May 4, 2022

(65) Prior Publication Data

US 2022/0370458 A1 Nov. 24, 2022

Related U.S. Application Data

(60) Provisional application No. 63/320,991, filed on Mar. 17, 2022, provisional application No. 63/184,710, filed on May 5, 2021.

(51) Int. Cl.
*A61K 31/519* (2006.01)
*A61K 31/506* (2006.01)
*A61P 35/00* (2006.01)

(52) U.S. Cl.
CPC .......... *A61K 31/519* (2013.01); *A61K 31/506* (2013.01); *A61P 35/00* (2018.01)

(58) Field of Classification Search
CPC ...... A61K 31/519; A61K 31/506; A61P 35/00
See application file for complete search history.

(56) References Cited

U.S. PATENT DOCUMENTS

| | | | |
|---|---|---|---|
| 9,815,813 B2 | 11/2017 | Chen et al. | |
| 10,077,276 B2 | 9/2018 | Chen et al. | |
| 10,280,171 B2 | 5/2019 | Jones et al. | |
| 10,287,266 B2 | 5/2019 | Chen et al. | |
| 10,561,655 B2 | 2/2020 | Xie et al. | |
| 10,590,090 B2 | 3/2020 | Koltun et al. | |
| 10,858,359 B2 | 12/2020 | Ma et al. | |
| 10,934,285 B2 | 3/2021 | Chen et al. | |
| 10,968,235 B2 | 4/2021 | Chen et al. | |
| 10,988,466 B2 | 4/2021 | Ma et al. | |
| 2019/0343836 A1 | 11/2019 | Alghalandis et al. | |
| 2021/0101870 A1 | 4/2021 | Koltun et al. | |
| 2022/0241277 A1 | 8/2022 | Alghalandis et al. | |

FOREIGN PATENT DOCUMENTS

| | | | | |
|---|---|---|---|---|
| AU | 2017276457 B2 | 10/2019 | | |
| AU | 2018207464 B2 | 5/2020 | | |
| CA | 3132395 A1 | * | 9/2020 | ............. A61K 45/06 |
| CN | 105916845 A | 8/2016 | | |
| CN | 107922388 A | 4/2018 | | |
| CN | 109311848 A | 2/2019 | | |
| CN | 109415360 A | 3/2019 | | |
| WO | 2015107494 A1 | 7/2015 | | |
| WO | 2016203406 A1 | 12/2016 | | |
| WO | 2017211303 A1 | 12/2017 | | |
| WO | 2017216706 A1 | 12/2017 | | |
| WO | 2018013597 A1 | 1/2018 | | |
| WO | 2018130928 A1 | 7/2018 | | |
| WO | 2018172984 A1 | 9/2018 | | |
| WO | 2019051084 A1 | 3/2019 | | |
| WO | 2019075265 A1 | 4/2019 | | |
| WO | 2019126736 A1 | 6/2019 | | |
| WO | 2019152454 A1 | 8/2019 | | |
| WO | 2019182960 A1 | 9/2019 | | |
| WO | 2019199792 A1 | 10/2019 | | |
| WO | 2020165733 A1 | 8/2020 | | |
| WO | WO-2020165734 A1 | * | 8/2020 | ............. A61K 31/00 |
| WO | 2020177653 A1 | 9/2020 | | |
| WO | 2021061515 A1 | 4/2021 | | |
| WO | 2022/235822 A1 | 11/2022 | | |

OTHER PUBLICATIONS

Y. Sun, et al. Allosteric SHP2 Inhibitor, IACS-13909, Overcomes EGFR-Dependent and EGFR-Independent Resistance Mechanisms toward Osimertinib. Cancer Res Nov. 1, 2020; 80 (21): 4840-4853. https://doi.org/10.1158/0008-5472.CAN-20-1634. (Year: 2020).*
Mitsudomi, et al. (2010), Epidermal growth factor receptor in relation to tumor development: EGFR gene and cancer. The FEBS Journal, 277: 301-308. https://doi.org/10.1111/j.1742-4658.2009.07448.x. (Year: 2010).*
Berge S.M., et al., "Pharmaceutical Salts," Journal of Pharmaceutical Sciences, Jan. 1977, vol. 66, No. 1, pp. 1-19.
Chinese Search Report for CN Application No. 201910160960.7, mailed Mar. 8, 2021, 2 pages.
Extended European Search Report for European Application No. 20766519.1, mailed Jan. 18, 2023, 12 Pages.
First Office Action for Chinese Application No. 201910160960.7, mailed Mar. 16, 2021, 9 Pages, English Translation.
Guo L., et al., "Puma Mediates the Anti-cancer Effect of Osimertinib In Colon Cancer Cells," OncoTargets and Therapy, Jan. 1, 2017, vol. 10, pp. 5281-5288, DOI: 10.2147/OTT.S139382, XP093004905.
International Preliminary Report on Patentability for International Application No. PCT/CN2020/077391, mailed Sep. 16, 2021, 14 Pages.
International Search Report and Written Opinion for International Application No. PCT/CN2020/077391, mailed Jun. 8, 2020, 26 Pages.
International Search Report and Written Opinion for International Application No. PCT/US2022/027693, mailed Aug. 10, 2022, 13 Pages.
International Search Report and Written Opinion for International Application No. PCT/US2022/027696, mailed Aug. 10, 2022, 13 Pages.

(Continued)

*Primary Examiner* — James H Alstrum-Acevedo
*Assistant Examiner* — Manahil Mirghani Ali Abdalhameed
(74) *Attorney, Agent, or Firm* — Womble Bond Dickinson (US) LLP

(57) ABSTRACT

Provided herein are SHP2 inhibitors for use in the reduction of solid tumors in a method of treating cancer.

26 Claims, 16 Drawing Sheets

(56) References Cited

OTHER PUBLICATIONS

International Search Report and Written Opinion for International Application No. PCT/US2022/027703, mailed Aug. 3, 2022, 10 Pages.
Lamarche M.J., et al., "Identification of TNO155. An Allosteric SHP2 Inhibitor for the Treatment of Cancer," Journal of Medicinal Chemistry, Sep. 1, 2020, vol. 63, No. 22, pp. 13578-13594, DOI: 10.1021/acs.jmedchem.0c01170, XP002803837.
Pai S.I., et al., "Molecular Pathology of Head and Neck Cancer: Implications for Diagnosis, Prognosis, and Treatment," Annual Review of Pathology: Mechanisms of Disease, Annual Reviews, US, Feb. 1, 2009, vol. 4, No. 1, pp. 49-70, DOI: 10.1146/annurev.pathol.4.110807.092158, ISSN 1553-4006, XP093004900.
Partial Supplementary European Search Report for European Application No. 20766519.1, mailed Oct. 25, 2022, 12 Pages.
International Preliminary Report on Patentability received for PCT Patent Application No. PCT/US2022/027703, mailed on Nov. 16, 2023, 8 pages.

* cited by examiner

G1: Vehicle
G2: Isotype Control
G3: Anti-PD1
G4: HBI-2376
G5: TNO-155
G6: RMC-4550

G1: Vehicle
G2: Isotype Control
G3: Anti-PD1
G4: HBI-2376
G5: TNO-155
G6: RMC-4550

G1: Vehicle
G2: Isotype Control
G3: Anti-PD1
G4: HBI-2376
G5: TNO-155
G6: RMC-4550

G1: Vehicle
G2: Isotype Control
G3: Anti-PD1
G4: HBI-2376
G5: TNO-155
G6: RMC-4550

G1: Vehicle
G2: Isotype Control
G3: Anti-PD1
G4: HBI-2376
G5: TNO-155
G6: RMC-4550

G1: Vehicle
G2: Isotype Control
G3: Anti-PD1
G4: HBI-2376
G5: TNO-155
G6: RMC-4550

| Absolute IC50 (µM) | | |
|---|---|---|
| | HCC827-ER1 | NCI-H1975 (L858R/T790M/C797S) |
| GH21001 (TNO-155) | 1.69 | >10 |
| GH21005 (HBI-2376) | 0.08 | 0.96 |
| RMC-4550 | 1.23 | >10 |
| Osimertinib | 2.8 | 2.43 |
| Cisplatin | 7.17 | 10.33 |

(HCC827 CDX)

(HCC827 CDX)

(DUSP6)

(10 day treatment at 10 mg/kg)

(10 day treatment at 10 mg/kg)

Normalized DUSP6/β-actin in HCC827 CDX models
(10 days treatment)

Normalized p-ERK/β-actin in HCC827 CDX models
(10 days treatment)

SHP2 INHIBITOR MONOTHERAPY AND USES THEREOF

CROSS-REFERENCE

This application claims the benefit of U.S. Provisional Application No. 63/184,710 filed May 5, 2021, and U.S. Provisional Application No. 63/320,991 filed Mar. 17, 2022, the contents of which are incorporated herein by reference in their entirety.

FIELD OF THE DISCLOSURE

The present disclosure relates to SHP2 inhibitors and methods of treating cancer.

BACKGROUND OF THE DISCLOSURE

Cancer is a significant cause of morbidity and mortality worldwide. While the standards of care for different cancer types have greatly improved over the years, current standards of care still fail to meet the need for effective therapies to improve treatment of cancer. Protein tyrosine phosphatase 2 (SHP2) belongs to the protein tyrosine phosphatase family, which is involved in regulating cell proliferation, survival, differentiation, migration and apoptosis. In the protein tyrosine phosphatase superfamily, SHP2 is the first true proto-oncogene to be confirmed, and it plays an important role in a variety of signaling pathways such as metabolism, differentiation, proliferation, migration and survival. SHP2 can regulate Ras-mitogen-activated protein kinase, Janus kinase-signal transducer and activator of transcription (JAK-STAT) or phosphoinositide 3-kinase-AKT and nuclear factor κB (NF-κB) and other signaling pathways. SHP2 is also the main regulator of the immune checkpoint signaling pathway of programmed cell death protein-1 (PD-1) and B and T lymphocyte attenuation factor (BTLA), which may be related to tumor immunosuppression. In addition, SHP2 mutations rarely occur in tumors.

In recent years, SHP2, has been shown to play an important role in tumor inhibition, especially as the role of SHP2 in tumors has become increasingly clear. Therefore, inhibition of SHP2 has become a feasible anti-tumor strategy. There remains a need for new treatments as cancers become resistant or refractory.

BRIEF SUMMARY

Provided herein, are methods of treating cancer with a SHP2 inhibitor.

In an aspect, provided herein is a method of treating cancer in a patient in need thereof, the method comprising administering to the patient a therapeutically effective amount of a compound having the structure of Formula (Ia), or a pharmaceutically acceptable salt or solvate thereof:

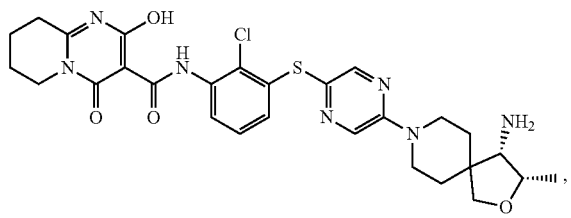

(Ia)

wherein the patient has failed an anti-cancer agent therapy.

In some embodiments, the method comprises administering the compound to the patient as third, fourth, fifth, or sixth line of treatment. In some embodiments, the cancer is resistant to at least one anti-cancer agent. In some embodiments, the anti-cancer agent is an immune checkpoint inhibitor. In some embodiments, the immune checkpoint inhibitor is PD-1, PD-L1, and/or CTLA-4. In some embodiments, the anti-cancer agent is an EGFR TK inhibitor. In some embodiments, the EGFR TK inhibitor is selected from erlotinib, afatinib, gefitinib, osimertinib, dacomitinib, icotinib, rociletinib, olmitinib, tarloxitinib, TAK-788, amivantamb (JNJ-6372), or AC00010. In some embodiments, the EGFR TK inhibitor is osimertinib.

In some embodiments, about 5 mg to about 100 mg of the compound of Formula (Ia), or a pharmaceutically acceptable salt or solvate thereof is administered to the patient in need thereof. In some embodiments, about 5 mg, about 10 mg, about 20 mg, about 30 mg, about 40 mg, or about 50 mg of the compound of Formula (Ia), or a pharmaceutically acceptable salt or solvate thereof is administered to the patient.

In some embodiments, the compound of Formula (Ia), or a pharmaceutically acceptable salt or solvate thereof, is administered as a regimen. In some embodiments, the compound of Formula (Ia) is administered orally or by intraperitoneal methods. In some embodiments, the compound of Formula (Ia) is administered daily. In some embodiments, the compound is administered to the patient once per day (QD), twice daily (BID), or three times per day (TID). In some embodiment, the compound of Formula (Ia) is administered for 7 days, 14 days, or 21 days.

In some embodiments, the cancer is squamous cell carcinoma, non-squamous cell carcinoma, non-small cell lung cancer (NSCLC), small cell lung cancer, melanoma, hepatocellular carcinoma, renal cell carcinoma, ovarian cancer, head and neck cancer, urothelial cancer, breast cancer, prostate cancer, glioblastoma, colorectal cancer, pancreatic cancer, lymphoma, leiomyosarcoma, liposarcoma, synovial sarcoma, or malignant peripheral sheath tumor (MPNST).

In some embodiments, the method of treating cancer inhibits metastasis of the cancer in the patient. In some embodiments, the method of treating cancer prolongs the time of disease progression in a cancer patient. In some embodiments, the method of treating cancer prolongs the survival of the patient. In some embodiments, the method of treating cancer increases progression-free survival of the patient. In some embodiments, the method of treating cancer reduces tumor or tumor burden in the patient.

In another aspect, provided herein is a method of decreasing tumor volume in a patient in need thereof, comprising administering to the patient a therapeutically effective amount of a compound having the structure of Formula (Ia), or a pharmaceutically acceptable salt or solvate thereof:

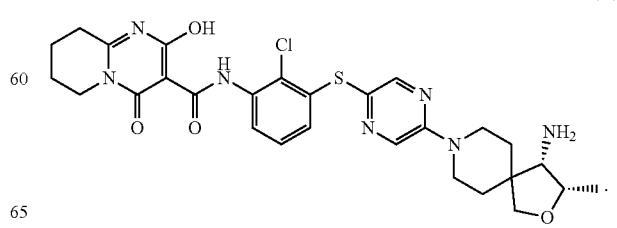

(Ia)

In some embodiments, the tumor volume is decreased by about 10%, about 20%, about 30%, about 40%, 50%, about 60%, about 70%, about 80%, or about 90%. In some embodiments, the tumor volume is decreased by at least about 10%.

In another aspect, presented herein is a method of modulating one or more biomarkers (cytokines) selected from INF-γ, IL-1β, IL-2, IL-4, IL-5, IL-6, IL-10, IL-12p70, and KC/GRO (CXCL1). In some embodiments, the one or more biomarkers increased or lowered over baseline levels. In some embodiments, the one or more biomarkers is lowered or increased by at least 5%, at least 10%, at least 15%, at least 20%, at least 25%, at least 30%, at least 40%, at least 50%, at least 100%, or at least 150%. In some embodiments, the one or more biomarkers is lowered or increased by at least 1.5 times, 2 times, 3 times, 4 times, 5 times, 10 times, 15 times, 20 times, or 25 times.

Other objects, features and advantages of the combinations and methods described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings below.

DETAILED DESCRIPTION

Methods of Treating Cancer

Figure 1:
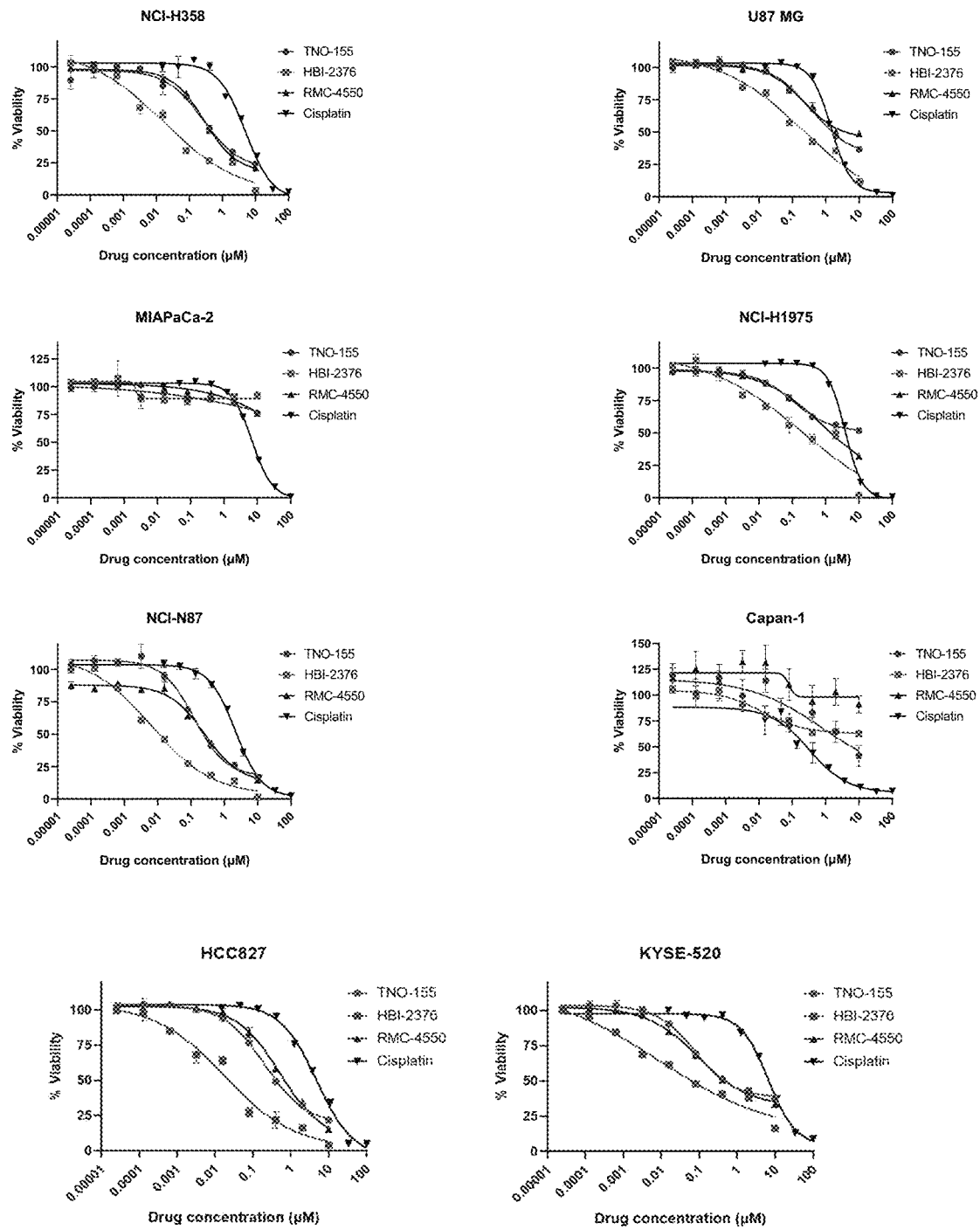
FIG. 1 shows that Compound (Ia) demonstrates greater potency in cell proliferation assays than other agents including GH21001 (TNO-155), RMC-4550, and Cisplatin.

In one aspect, described herein is a method of treating cancer in a patient in need thereof, the method comprising administering to the patient a therapeutically effective amount of a compound having the structure of Formula (I), or a pharmaceutically acceptable salt or solvate thereof:

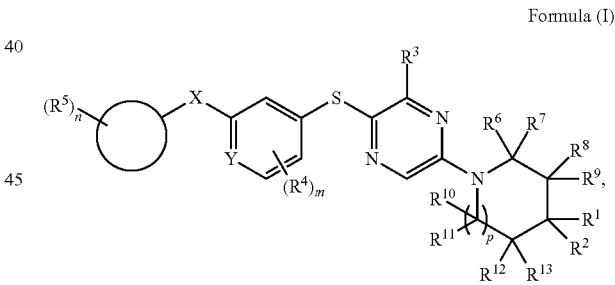

Formula (I)

wherein,
$R^1$ and $R^2$ are each the same or different, and they are each independently selected from H, D, halogen, —CN, —C(O)OH, —CHO, —OH, —NO$_2$, and the following substituted or unsubstituted groups: —NH$_2$, $C_1$-$C_{10}$ alkyl, $C_1$-$C_{10}$ alkylamino, $C_1$-$C_{10}$ alkoxy, $C_3$-$C_{12}$ cycloalkyl, $C_3$-$C_{12}$ cycloalkyloxy, 3-12 membered heterocyclic group, $C_6$-$C_{10}$ aryl group, 5-10 membered heteroaryl group; or $R^1$ and $R^2$ form a 3-8 membered saturated or unsaturated cycloalkyl or heterocyclic group, optionally, the 3-8 membered saturated or unsaturated cycloalkyl or heterocyclic group has one to three —OH, —NH$_2$, —CN, NO$_2$, halogen, $C_1$-$C_{10}$ alkyl, $C_1$-$C_{10}$ alkaneoxy, $C_1$-$C_{10}$ alkylamino, $C_3$-$C_{12}$ cycloalkyl, $C_6$-$C_{10}$ aryl or 5-10 membered heteroaryl;
$R^3$ is selected from H, D, or —NH$_2$;
X is selected from a bond, —NH—, or —C(O)NH—;

Y is selected from N or $CR^{13}$, wherein $R^{13}$ is selected from H, D, —OH, —CN, halogen, $C_1$-$C_{10}$ alkyl group, $C_1$-$C_{10}$ alkoxy, $C_3$-$C_{12}$ cycloalkane amino, $C_1$-$C_{10}$ alkylamino, $C_3$-$C_{12}$ cycloalkyl, 3-8 membered heterocyclic group, halogenated $C_1$-$C_{10}$ alkylamino, or $C_6$-$C_{10}$ aryl or 5-10 membered heteroaryl group, the heterocyclic group or heteroaryl group optionally contains one to four heteroatoms, and the heteroatoms are selected from S, O, N or NH;

each $R^4$ is the same or different, and is independently selected from H, D, halogen, —CN, —C(O)OH, —CHO, —OH, —NO$_2$, —C(O)NHR$^{14}$ or —NHC(O)R$^{15}$, substituted or unsubstituted with the following groups: —NH$_2$, $C_1$-$C_{10}$ alkyl, $C_1$-$C_{10}$ alkylamino, $C_1$-$C_{10}$ alkoxy, $C_3$-$C_{12}$ cycloalkyl, 3-12 membered heterocyclic group, $C_6$-$C_{10}$ aryl, or 5-10 membered heteroaryl; wherein $R^{14}$ and $R^{15}$ are each independently selected from $C_1$-$C_{10}$ alkylamino, $C_3$-$C_{12}$ cycloalkyl, $C_6$-$C_{10}$ aryl or 5-10 membered heteroaryl; the substitution is selected from $C_1$-$C_{10}$ alkyl, halogen atom, —NH$_2$, —CN, —C(O)OH, —CHO, —OH, —NO$_2$, $C_1$-$C_{10}$ alkoxy, $C_1$-$C_{10}$ alkylamino, $C_3$-$C_{12}$ cycloalkyl, $C_6$-$C_{10}$ aryl, 5-10 membered heteroaryl or 3-12 membered heterocyclic group is substituted by one or more substituents, the above-mentioned substituents are optionally substituted with one to three substituents selected from $C_1$-$C_{10}$ alkyl, halogen, —NH$_2$, —CN, —C(O)OH, —CHO, —OH, —NO$_2$, $C_1$-$C_{10}$ alkoxy, $C_1$-$C_{10}$ alkylamino, or $C_3$-$C_{12}$ cycloalkyl;

is selected from $C_6$-$C_{10}$ aryl, 5-10 membered heteroaryl, $C_4$-$C_{12}$ cycloalkyl, 3-12 membered heterocyclic group, $C_6$-$C_{14}$ bridged ring group or spiro ring group, or $C_6$-$C_{14}$ bridged heterocyclic group or spiro heterocyclic group; wherein the 5-10 membered heteroaryl, 3-12 membered heterocyclic group, $C_6$-$C_{14}$ bridged heterocyclic group or spiro heterocyclic group contains one to three heteroatoms or groups selected from N, NH, O, S, C(O), or S(O);

each $R^5$ is the same or different, and is independently selected from H, D, halogen, —CN, —C(O)OH, —CHO, —OH, —NO$_2$, aminoacyl, substituted or unsubstituted following groups: $C_1$-$C_{10}$ alkyl, $C_1$-$C_{10}$ alkylamino, $C_1$-$C_{10}$ alkoxy, —NH$_2$, $C_3$-$C_{12}$ cycloalkyl, 3-12 membered heterocyclic group, $C_6$-$C_{10}$ aryl or 5-10 membered heteroaryl, the substitution is selected from $C_1$-$C_{10}$ alkyl, $C_3$-$C_{12}$ cycloalkyl, 3-12 membered heterocyclic group, halogen, —NH$_2$, —CN, —C(O)OH, —CHO, —OH, —NO$_2$, hydroxy-$C_1$-$C_{10}$ alkyl, $C_1$-$C_{10}$ alkoxy, $C_1$-$C_{10}$ alkylamino, 5-10 membered heteroaromatic group, $C_6$-$C_{10}$ aryl group or 3-12 membered heterocyclic group substituted by one or more substituents; or any two adjacent $R^5$ form a 3-6 membered saturated or unsaturated ring, and optionally the 3-6 membered saturated or unsaturated ring is substituted with one to three —OH, —NH$_2$, —CN, halogen, $C_1$-$C_{10}$ alkyl, $C_1$-$C_{10}$ alkoxy, $C_3$-$C_{12}$ cycloalkylamino, $C_1$-$C_{10}$ alkylamino, $C_3$-$C_{12}$ cycloalkyl, halogenated $C_1$-$C_{10}$ alkylamino, $C_6$-$C_{10}$ aryl or 5-10 member heteroaryl;

$R^6$, $R^7$, $R^8$, $R^9$, $R^{10}$, $R^{11}$, $R^{12}$, and $R^{13}$ are each independently selected from H, D, halogen, —CN, —C(O)OH, —CHO, —OH, —NO$_2$, substituted or unsubstituted the group selected from —NH$_2$, $C_1$-$C_{10}$ alkyl, $C_1$-$C_{10}$ alkylamino, $C_1$-$C_{10}$ alkoxy, $C_3$-$C_{12}$ cycloalkyl, $C_3$-$C_{12}$ cycloalkyloxy group, 3-12 membered heterocyclic group, $C_6$-$C_{10}$ aryl, and 5-10 membered heteroaryl, the substitution is selected from $C_1$-$C_{10}$ alkyl, $C_3$-$C_{12}$ cycloalkyl, 3-12 membered heterocyclic group, halogen, —NH$_2$, —CN, —C(O)OH, —CHO, —OH, —NO$_2$, hydroxy-$C_1$-$C_{10}$ alkyl, $C_1$-$C_{10}$alkoxy, $C_1$-$C_{10}$ alkylamino, 5-10 membered heteroaryl or $C_6$-$C_{10}$ aryl;

m is 0, 1, 2 or 3;

n is 0, 1, 2 or 3; and p is 0, 1, or 2; and wherein the patient in need of cancer treatment has failed at least one anti-cancer agent therapy. In some embodiments, the patient in need of cancer treatment has previously received anti-cancer agent therapy (i.e., has been previously treated with at least one anti-cancer agent) that has failed to achieve at least one end point of successful anti-cancer therapy. In some embodiments, the previous anti-cancer agent therapy failed to achieve tumor remission or progression-free survival of the patient.

In some embodiments, the method comprises administering the compound to the patient as third, fourth, fifth, or sixth line of treatment. In some embodiments, the cancer is resistant to at least one anti-cancer agent. In some embodiments, the anti-cancer agent is an immune checkpoint inhibitor. In some embodiments, the immune checkpoint inhibitor is PD-1, PD-L1, and/or CTLA-4. In some embodiments, the anti-cancer agent is an EGFR TK inhibitor. In some embodiments, the EGFR TK inhibitor is selected from erlotinib, afatinib, gefitinib, osimertinib, dacomitinib, icotinib, rociletinib, olmatinib, tarloxotinib, TAK-788, amivantamab (JNJ-6372), or AC0010. In some embodiments, the EGFR TK inhibitor is osimertinib.

In some embodiments, the compound of Formula (I) has the structure of Formula (II), or a pharmaceutically acceptable salt or solvate thereof:

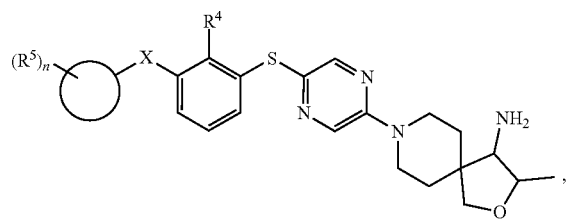

Formula (II)

wherein,

X is selected from chemical bond, —NH—, —CONH—;

$R^4$ is selected from H, D, halogen atom, —CN, —C(O)OH, —CHO, —OH, —NO$_2$, —C(O)NHR$^{14}$ or —NHC(O)R$^{15}$, substituted or unsubstituted with the group selected from —NH$_2$, $C_1$-$C_{10}$ alkyl, $C_1$-$C_{10}$ alkylamino, $C_1$-$C_{10}$ alkoxy, $C_3$-$C_{12}$ cycloalkyl, 3-12 membered heterocyclic group, $C_6$-$C_{10}$ aryl, or 5-10 membered heteroaryl; wherein $R^{14}$ and $R^{15}$ are each independently selected from $C_1$-$C_{10}$ alkylamino, $C_3$-$C_{12}$ cycloalkyl, $C_6$-$C_{10}$ aryl or 5-10 membered heteroaryl group; the substituent is selected from $C_1$-$C_{10}$ alkyl, halogen, —NH$_2$, —CN, —C(O)OH, —CHO, —OH, —NO$_2$, or $C_1$-$C_{10}$ alkoxy, substituted by one or more substituents of $C_1$-$C_{10}$ alkylamino, $C_3$-$C_{12}$ cycloalkyl, $C_6$-$C_{10}$ aryl, 5-10 membered heteroaryl, or 3-12 membered heterocyclic group, the substituents are optionally selected from $C_1$-$C_{10}$ alkyl, halogen, —$NH_2$, —CN, —C(O)OH, —CHO, —OH, —$NO_2$, $C_1$-$C_{10}$ alkoxy, $C_1$-$C_{10}$ alkylamino, or $C_3$-$C_{12}$ cycloalkyl;

○ is selected from $C_6$-$C_{10}$ aryl, 5-10 membered heteroaryl, $C_4$-$C_{12}$ cycloalkyl, 3-12 membered heterocyclic group, $C_6$-$C_{14}$ bridged ring group or spiro ring group, or $C_6$-$C_{14}$ bridged heterocyclic group or spiro heterocyclic group; wherein the 5-10 membered heteroaryl group, 3-12 membered heterocyclic group, $C_6$-$C_{14}$ bridged heterocyclic group or spiro heterocyclic group contains one to three heteroatom or groups selected from N, NH, O, S, C(O), or S(O);

each $R^5$ is the same or different, and is independently selected from H, D, halogen atom, —CN, —C(O)OH, —CHO, —OH, —$NO_2$, or aminoacyl, substituted or unsubstituted with the group selected from $C_1$-$C_{10}$ alkyl, $C_1$-$C_{10}$ alkylamino, $C_1$-$C_{10}$ alkoxy, —$NH_2$, $C_3$-$C_{12}$ cycloalkyl, 3-12 membered heterocyclic group, $C_6$-$C_{10}$ aryl or 5-10 membered heteroaryl, the substituent selected from $C_1$-$C_{10}$ alkyl, $C_3$-$C_{12}$ cycloalkyl, 3-12 membered heterocyclic group, halogen, —$NH_2$, —CN, —C(O)OH, —CHO, —OH, —$NO_2$, hydroxy-$C_1$-$C_{10}$ alkyl, $C_1$-$C_{10}$ alkoxy, $C_1$-$C_{10}$ alkylamino, 5-10 membered heteroaromatic group, $C_6$-$C_{10}$ aryl or 3-12 membered heterocyclic group substituted by one or more substituents; or any two adjacent $R^5$ form a 3-6 membered saturated or unsaturated ring, and is optionally, the 3-6 membered saturated or unsaturated ring is comprises one to three —OH, —$NH_2$, —CN, halogen, $C_1$-$C_{10}$ alkyl, $C_1$-$C_{10}$ alkoxy, $C_3$-$C_{12}$ cycloalkylamino, $C_1$-$C_{10}$ alkylamino, $C_3$-$C_{12}$ cycloalkyl, halogenated $C_1$-$C_{10}$ alkylamino, $C_6$-$C_{10}$ aryl or 5-10 member heteroaryl; and n is 0, 1, 2 or 3;

In some embodiments, $R^4$ is selected from H, D, halogen, —CN, unsubstituted or halogen atom substituted $C_1$-$C_{10}$ alkyl.

In some embodiments,

○ is elected from phenyl, naphthyl, 5-10 membered heteroaryl or 3-12 membered heterocyclic group; wherein the 5-10 membered heteroaryl group and 3-12 membered heterocyclic group contain one to three heteroatoms or groups optionally selected from N, NH, O, S, or C(O).

In some embodiments, the 5-10 membered heteroaromatic ring is selected from thienyl; pyridyl; pyrimidinyl; pyrazinyl; pyridazinyl; pyrrolyl; pyrazolyl; thiazolyl; 1,2,3-triazolyl; 1,2,4-triazolyl; imidazolyl; tetrazolyl; isothiazolyl; oxazolyl; isoxazolyl; thiadiazolyl; oxadiazolyl; benzothienyl; indolyl; benzimidazolyl; benzothiazolyl; benzofuranyl; quinolinyl; isoquinolinyl; quinazolinyl; indazolyl; indole[1,2-a]pyrimidinyl; 4,7-diazaindole; pyrazolopyrimidinyl; imidazopyrimidinyl; oxazolopyrimidinyl; isoxazolopyrimidiny; imidazopyrazinyl; pyrazolopyrazine; pyrrolopyrazinyl; or furan. In some embodiments, any one of pyrazinyl, thienopyrazinyl, pyridopyrimidinone, benzoxazolyl, and benzothiazolyl; the 3-12 membered heterocyclic group is selected from aziridinyl, oxetanyl, pyrrolidinyl, tetrahydrofuranyl, tetrahydrothienyl, piperidinyl, morpholinyl, piperazinyl, thiomorpholinyl, tetrahydropyranyl, 1,1-dioxythiomorpholinyl, butyrolactam, valerolactam, caprolactam, butyrolactone, valerolactone, caprolactone, succinimide or

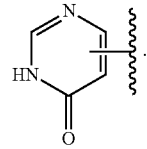

In some embodiments, the 3-12 membered heterocyclic group is selected from butyrolactamyl, pyrrolidinyl, succinimide, or

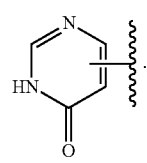

In some embodiments, each $R^5$ is the same or different, and is independently selected from H, D, halogen, —CN, —C(O)OH, —CHO, —OH, —$NO_2$, aminoacyl, substituted or unsubstituted with a $C_1$-$C_{10}$ alkyl, $C_1$-$C_{10}$ alkylamino, $C_1$-$C_{10}$ alkoxy, —$NH_2$, and the substitution is selected from $C_1$-$C_{10}$ alkyl, halogen, —$NH_2$, —CN, —OH, —$NO_2$ are substituted by one or more substituents; or any two adjacent $R^5$ form a 3-6 membered saturated or unsaturated ring, optionally, the 3-6-membered saturated or unsaturated ring is substituted with one to three —OH, —$NH_2$, —CN, halogen, $C_1$-$C_{10}$ alkyl, and $C_1$-$C_{10}$ alkoxy.

In some embodiments, the compound of Formula (I) has the structure of Formula (Ia), or a pharmaceutically acceptable salt or solvate thereof:

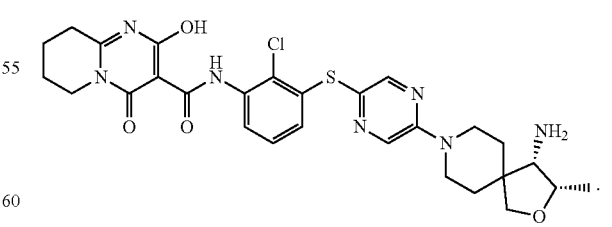

(Ia)

In another aspect, provided herein is a method of decreasing tumor volume in a patient in need thereof, comprising administering to the patient a therapeutically effective amount of a compound having the structure of Formula (Ia), or a pharmaceutically acceptable salt or solvate thereof:

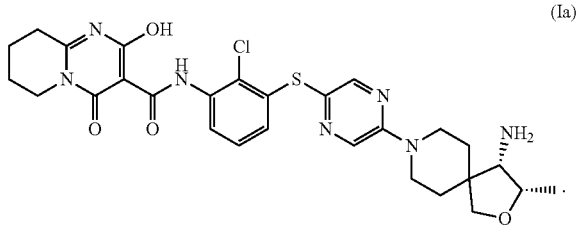 [SMILES: C[C@@H]1OCC2(CCN(c3cnc(Sc4cccc(NC(=O)c5c(O)nc6n(c5=O)CCCC6)c4Cl)cn3)CC2)[C@@H]1N]

(Ia)

In some embodiments, the compound of Formula (I) or (Ia) is N-(3-((5-((3S,4S)-4-amino-3-methyl-2-oxa-8-azaspiro[4.5]decan-8-yl)pyrazin-2-yl)thio)-2-chlorophenyl)-2-hydroxy-4-oxo-6,7,8,9-tetrahydro-4H-pyrido[1,2-a]pyrimidine-3-carboxamide, or a pharmaceutically acceptable salt or solvate thereof.

Any combination of the groups described above for the various variables is contemplated herein. Throughout the specification, groups and substituents thereof are chosen by one skilled in the art to provide stable moieties and compounds.

The compound(s) of Formula (I), (Ia), or (II), or a pharmaceutically acceptable salt or solvate thereof is a SHP2 inhibitor. The compound(s) of Formulas (I), (Ia) and (II) are substantially described by International Patent Application No. PCT/CN2020/077391, filed Mar. 2, 2020, which is incorporated herein by reference in its entirety.

Dosage

In some embodiments, the method comprises administering to the patient in need about 1 mg, 2 mg, 3 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 125 mg, 150 mg, 175 mg, 200 mg, 225 mg, 250 mg, 275 mg, 300 mg, 325 mg, 350 mg, 375 mg, 400 mg, 425 mg, 450 mg, 475 mg, or 500 mg of the compound of Formula (I), (e.g., a compound of Formula (Ia)), or a pharmaceutically acceptable salt or solvate thereof. In some embodiments, the method comprises administering to the patient about 100 mg, 150 mg, or about 200 mg of the compound of Formula (I). In some embodiments, the method comprises administering from about 1 mg to about 500 mg or from about 1 mg to about 200 mg of the compound of Formula (I). In some embodiments, the method comprises administering from about 1 mg to about 10 mg, from about 1 mg to about 25 mg, from about 1 mg to about 50 mg, from about 5 mg to about 10 mg, from about 5 mg to about 25 mg, from about 5 mg to about 50 mg, from about 10 mg to about 25 mg, from about 10 mg to about 50 mg, from about 50 mg to about 100 mg, from about 100 mg to about 200 mg, or from about 200 mg to about 500 mg of the compound of Formula (I).

In some embodiments, the method comprises administering to the patient in need thereof, a dose of at least about 1 mg, 2 mg, 3 mg, 4 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 gm, 80 mg, 85 mg, 90 mg, 95 mg, 100 mg, 125 mg, 150 mg, 175 mg, or 200 mg of the compound of Formula (I), or a pharmaceutically acceptable salt or solvate thereof (e.g., a compound of Formula (Ia)). In some embodiments, the method comprises administering to the patient at least about 1 mg, 2 mg, 3 mg, 4 mg, 5 mg, 6 mg, 7 mg, 8 mg, 9 mg, or 10 mg of the compound of Formula (I). In some embodiments, the method comprises administering to the patient in need about 100 mg, about 150 mg, or about 200 mg of a compound of Formula (I). In some embodiments, the method comprises administering to the patient in need, from about 1 mg to about 10 mg, from about 1 mg to about 25 mg, from about 1 mg to about 50 mg, from about 5 mg to about 10 mg, from about 5 mg to about 25 mg, from about 5 mg to about 50 mg, from about 10 mg to about 25 mg, from about 10 mg to about 50 mg, from about 50 mg to about 100 mg, or from about 100 mg to about 200 mg of the compound of Formula (I).

In some embodiments, the method comprises administering from about 5 mg to about 500 mg or from about 5 mg to about 200 mg of the compound of Formula (I), or a pharmaceutically acceptable salt or solvate thereof. In some embodiments, the method comprises administering to the patient in need about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, or about 200 mg of the compound of Formula (I).

In some embodiments, the method comprises administering to the patient in need thereof, a compound of Formula (I), or a pharmaceutically acceptable salt or solvate thereof (e.g., Formula (Ia)) in an amount relative to the weight of the patient (i.e., mg/kg). In some instances, the method comprises administering to the patient in need thereof, a compound of Formula (I) in an amount equivalent from about 0.0001 mg/kg to about 200 mg/kg, 0.001 mg/kg to about 200 mg/kg, 0.01 mg/kg to about 200 mg/kg, 0.01 mg/kg to about 150 mg/kg, 0.01 mg/kg to about 100 mg/kg, 0.01 mg/kg to about 50 mg/kg, 0.01 mg/kg to about 25 mg/kg, 0.01 mg/kg to about 10 mg/kg, or 0.01 mg/kg to about 5 mg/kg, 0.05 mg/kg to about 200 mg/kg, 0.05 mg/kg to about 150 mg/kg, 0.05 mg/kg to about 100 mg/kg, 0.05 mg/kg to about 50 mg/kg, 0.05 mg/kg to about 25 mg/kg, 0.05 mg/kg to about 10 mg/kg, or 0.05 mg/kg to about 5 mg/kg, 0.5 mg/kg to about 200 mg/kg, 0.5 mg/kg to about 150 mg/kg, 0.5 mg/kg to about 100 mg/kg, 0.5 mg/kg to about 50 mg/kg, 0.5 mg/kg to about 25 mg/kg, 0.5 mg/kg to about 10 mg/kg, or 0.5 mg/kg to about 5 mg/kg per body weight. In some embodiments, the method comprises administering to the patient in need thereof from about 1 mg/kg to about 200 mg/kg, from about 1 mg/kg to about 150 mg/kg, from about 1 mg/kg to about 100 mg/kg, from about 1 mg/kg to about 50 mg/kg, from about 1 mg/kg to about 25 mg/kg, from about 1 mg/kg to about 10 mg/kg, or from about 1 mg/kg to about 5 mg/kg of a compound of Formula (I).

In some embodiments, the method comprises administering to the patient in need thereof, from about 5 mg/kg to about 25 mg/kg per patient body weight of the patient, of a compound of Formula (I), or a pharmaceutically acceptable salt or solvate thereof (e.g., a compound of Formula (Ia)). In some embodiments, the method comprises administering to the patient in need about 5 mg/kg, about 10 mg/kg, about 15 mg/kg, about 20 mg/kg, or about 25 mg/kg per body weight of the patient, of a compound of Formula (I).

Further Forms of Compounds

In some embodiments, a compound disclosed herein possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming of diastereomeric salts and separation by recrystallization, or chromatography, or any combination thereof. Jean Jacques, Andre Collet, Samuel H. Wilen, "Enantiomers, Racemates and Resolutions," John Wiley and Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In some embodiments, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design of prodrugs of the compound is possible. (See, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., *Pharmacological Reviews*, 56:53-102, 2004; Aesop Cho, "Recent Advances in Oral Prodrug Discovery," *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

In some embodiments, some of the compounds described herein may be a prodrug for another derivative or active compound.

In some embodiments, sites on the aromatic ring portion of compounds described herein are susceptible to various metabolic reactions. Therefore, incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g., with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine, chlorine, and iodine such as, for example, $^2$H, $^3$H, $^{13}$C, $^{14}$C, $^{15}$N, $^{18}$O, $^{17}$O, $^{35}$S, $^{18}$F, $^{36}$Cl, and $^{125}$I. In some embodiments, isotopically labeled compounds described herein, for example those into which radioactive isotopes such as $^3$H and $^{14}$C are incorporated, are useful in drug and/or substrate tissue distribution assays. In some embodiments, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration in an organism in need thereof, to produce a metabolite that is then used to produce a desired effect, including a desired therapeutic effect.

"Pharmaceutically acceptable" as used herein, refers to a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound disclosed herein with acids. Pharmaceutically acceptable salts are also obtained by reacting a compound disclosed herein with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g., lithium, sodium, potassium), an alkaline earth ion (e.g., magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

In some embodiments, a pharmaceutically acceptable salt includes the solvent addition forms, particularly solvates. Solvates contain either stoichiometric or non-stoichiometric amounts of a solvent and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Pharmaceutical Compositions

In one aspect, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the chosen route of administration. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999), herein incorporated by reference for such disclosure.

A pharmaceutical composition, as used herein, refers to a mixture of a compound disclosed herein with other chemical components (i.e., pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administrable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds disclosed herein are administered orally.

In some embodiments, the pharmaceutical formulation is in the form of a tablet. In other embodiments, pharmaceutical formulations of the compounds disclosed herein are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound disclosed herein is formulated for use as an aerosol, a mist or a powder.

For buccal or sublingual administration, the compositions may take the form of tablets, lozenges, or gels formulated in a conventional manner.

In some embodiments, compounds disclosed herein are prepared as transdermal dosage forms.

In one aspect, a compound disclosed herein is formulated into a pharmaceutical composition suitable for intramuscular, subcutaneous, or intravenous injection.

In some embodiments, the compound disclosed herein is administered topically and can be formulated into a variety of topically administrable compositions, such as solutions, suspensions, lotions, gels, pastes, medicated sticks, balms, creams or ointments.

In some embodiments, the compounds disclosed herein are formulated in rectal compositions such as enemas, rectal gels, rectal foams, rectal aerosols, suppositories, jelly suppositories, or retention enemas.

Pharmaceutical compositions and dosage forms described herein typically include one or more excipients. Suitable excipients are well known to those skilled in the art of pharmacy. Whether a certain excipient is suitable for incorporation into a pharmaceutical composition or dosage form depends on a variety of factors such as, for example, the intended route of administration to the patient. Pharmaceutical compositions described herein can include other agents such as stabilizers, lubricants, buffers, and disintegrants that can reduce the rate by which an active ingredient can decompose in a certain formulation.

Pharmaceutical compositions described herein can in certain instances include additional active agents other than those in the combinations described herein (e.g., an anti-cancer agent such as those described herein) in an amount provided herein.

In some embodiments, the compounds of Formula (I) are provided in an oral dosage form such as a tablet or capsule. In some embodiment, the compounds of Formula (I) are supplied as a powder (e.g., lyophilized powder) that can be resuspended in a liquid suitable for parenteral administration. In some embodiments, the compound of formula (I) are formulated for intravenous (I.V.) administration.

In some embodiments, the compounds described herein can be provided as controlled release pharmaceutical products, which have a goal of improving drug therapy over that achieved by their non-controlled counterparts. Controlled release formulations can extend activity of the drug, reduce dosage frequency, and increase subject compliance. In addition, controlled release formulations can be used to affect the time of onset of action or other characteristics, such as blood levels of the drug, and can thus affect the occurrence of side (e.g., adverse) effects.

Cancers

The compounds and pharmaceutical compositions described herein are useful for treating diseases, disorders, or alleviating or eliminating the symptoms of diseases and disorders such as, for example, cancer.

In some embodiments, the cancer is in the form of a tumor. In some embodiments, the cancer is selected from squamous cell carcinoma, non-squamous cell carcinoma, non-small cell lung cancer (NSCLC), small cell lung cancer, melanoma, hepatocellular carcinoma, renal cell carcinoma, ovarian cancer, head and neck cancer, urothelial cancer, breast cancer, prostate cancer, glioblastoma, colorectal cancer, pancreatic cancer, lymphoma, leiomyosarcoma, liposarcoma, synovial sarcoma, or malignant peripheral sheath tumor (MPNST). In some embodiments, the cancer is squamous cell carcinoma. In some embodiments, the cancer is non-squamous cell carcinoma. In some embodiments, the cancer is non-small cell lung cancer (NSCLC). In some embodiments, the cancer is small cell lung cancer. In some embodiments, the cancer is melanoma. In some embodiments, the cancer is hepatocellular carcinoma. In some embodiments, the cancer is renal cell carcinoma. In some embodiments, the cancer is ovarian cancer. In some embodiments, the caner is head and neck cancer. In some embodiments, the cancer is urothelial cancer. In some embodiments, the cancer is breast cancer (e.g., HER2 negative or HER2 positive breast cancer). In some embodiments, the cancer is prostate cancer. In some embodiments, the cancer is glioblastoma. In some embodiments, the cancer is colorectal cancer. In some embodiments, the care is pancreatic cancer. In some embodiments, the cancer is lymphoma. In some embodiments, the cancer is synovial sarcoma. In some embodiments, the cancer is malignant peripheral sheath tumor (MPNST).

In some embodiments, the tumor is a solid tumor. In some embodiments, the method of treating cancer reduces the tumor volume or tumor burden in the patient. In some embodiments, the tumor is reduced in volume from 5% to 95% or 5% to 50% or any value therein. In some embodiments, the tumor is reduced in volume by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, or about 95%. In some embodiments, the tumor volume is reduced by about 90%, about 91%, about 92%, about 93%, about 94%, about 95%, about 96%, about 97%, about 98%, or about 99%.

In some embodiments, the tumor is reduced in volume by at least 5%, at least 10%, at least 20%, at least 30%, at least 40%, or at least 50%.

In some embodiments, the cancer is a hematological cancer. In some embodiments, the cancer is a hematological cancer selected from lymphoma, Non-Hodgkin's lymphoma (NHL), Hodgkin's Lymphoma, Reed-Sternberg disease, multiple myeloma (MM), acute myelogenous leukemia (AML), chronic myelogenous leukemia (CML), acute lymphocytic leukemia (ALL), or chronic lymphocytic leukemia (CLL). In some embodiments, the cancer is Hodgkin's Lymphoma or Reed-Sternberg disease.

In some embodiments, the cancer is lymphoma. In some embodiments, the cancer is Non-Hodgkin lymphoma (NHL). In some embodiments, the NHL is indolent NHL (e.g., follicular lymphoma (FL); lymphoplasmacytic lymphoma (LL); marginal zone lymphoma (MZL) or primary cutaneous anaplastic large cell lymphoma) or aggressive NHL (e.g., Diffuse large B-cell lymphoma (DLBCL); Follicular large cell lymphoma stage III; anaplastic large cell lymphoma; extranodal NK-/T-cell lymphoma; lymphomatoid granulmatosis; angioimmunoblastic T-cell lymphoma; peripheral T-cell lymphoma; intravascular large B-cell lymphoma; Burkitt lymphoma; lymphoblastic lymphoma; adult T-cell leukemia/lymphoma; or mantle cell lymphoma). In some embodiments, the cancer is Hodgkin's lymphoma (e.g., classical or nodular lymphocyte-predominant). In some embodiments, the Hodgkin's Lymphoma includes Reed-Sternberg cells and can cause Reed-Sternberg disease. In some embodiments, the cancer is multiple myeloma (MM). In some embodiments, the cancer is acute myelogenous leukemia (AML). In some embodiments, the cancer is chronic myelogenous leukemia (CML). In some embodiments, the cancer is chronic lymphocytic leukemia (CLL), (e.g., Binet Stage A cancer or a Binet Stage B cancer). In some embodiments, the cancer is acute lymphocytic leukemia (ALL), (e.g., T-cell or B-cell lymphoblastic leukemia).

In some embodiments, the cancer is a Stage I, Stage II, Stage, III, or Stage IV cancer. In some embodiments, the cancer is a Stage I cancer (e.g., Stage IA, IB, or IC). In some embodiments, the cancer is a Stage II cancer (e.g., Stage IIA or IIB). In some embodiments, the cancer is a Stage III cancer, (e.g., Stage IIIA, IIIB, or IIIC). In some embodiments, the cancer is a Stage IV cancer, (e.g., Stage IVA or IVB).

The treatments described herein can be administered to a cancer patient at any time following diagnosis. For example, the cancer patient can be treatment naive (i.e., has not received a cancer therapy for the diagnosed cancer). The cancer patient can be treatment naive for one cancer but can be diagnosed with one or more other cancers resulting from, for example, metastasis or malignancy. The cancer patient can be immune checkpoint naive for one or more cancers. The cancer patient can have a cancer that is refractory. In certain instances, the combinations described herein are administered as a first line therapy (e.g., the first therapy administered to a treatment naive cancer patient) to a patient in need thereof.

In some embodiments, the method of treating cancer inhibits metastasis of the cancer in the patient. In some embodiments, metastasis is inhibited by at least about 5%, 10%, 20%, 30%, 40%, 50%, 60%, 70%, 80%, 90%, or 100%.

In some embodiments, the method of treating cancer reduces pre-existing tumor metastasis in the patient. In some embodiments, preexisting tumor metastasis is reduced by at least about 5%, 10%, 20%, 30%, 40%, 50%, 60%, 70%, 80%, 90%, or 100%.

In some embodiments, the method of treating cancer prolongs or increases the time to disease progression of the cancer in the patient (including progression between advanced stages; e.g., progression from Stage III to Stage IV cancer). In some embodiments, the increase is a comparison between the time to disease progression with and without treatment. In some embodiments, the methods described herein prolong the time to disease progression by at least 1 week, 2 weeks, 3 weeks, 4 weeks, 1 month, 2 months, 3 months, 4 months, 5 months, 6 months, 7 months, 8 months, 9 months, 10 months, 11 months, 1 year, or more, including values therein.

In some embodiments, the method of treating cancer prolongs the survival of the patient. In some embodiments, the method of treating cancer increases progression-free survival of the patient. In some embodiments, the method of treating cancer prolongs the time to disease progression of the cancer in the patient. In some embodiments, the method of treating cancer prolongs the survival of the patient. In some embodiments, the method of treating cancer increases progression-free survival of the patient. In some embodiments, survival is prolonged by at least 1 week, 2 weeks, 3 weeks, 4 weeks, 1 month, 2 months, 3 months, 4 months, 5 months, 6 months, 7 months, 8 months, 9 months, 10 months, 11 months, 1 year, 2 years, or more, including values therein.

In some embodiments, the patient is treatment naive.

In some embodiments, the method comprises administering the compound of Formula (I), or a pharmaceutically acceptable salt or solvate thereof (e.g., a compound of Formula (Ia)), to the patient as a first line therapy. In some embodiments, the method comprises administering the compound of Formula (I), or a pharmaceutically acceptable salt or solvate thereof (e.g., a compound of Formula (Ia)), to the patient as a second, third, fourth, fifth, or sixth line of treatment. In some embodiments, the method comprises administering the compound of Formula (I) as a second line of treatment. In some embodiments, the method comprises administering the compound of Formula (I) as a third line of treatment. In some embodiments, the method comprises administering the compound of Formula (I), as a fourth line treatment.

In some embodiments, the method comprises administering the compound of Formula (I), or a pharmaceutically acceptable salt or solvate thereof (e.g., a compound of Formula (Ia)), to the patient following treatment with at least one anti-cancer therapy. In some embodiments, the anti-cancer therapy is chemotherapy, radiotherapy, surgery, targeted therapy, immunotherapy, or a combination thereof. In some embodiments, the anti-cancer therapy is chemotherapy. In some embodiments, the anti-cancer therapy is radiotherapy. In some embodiments, the anti-cancer therapy is cancer surgery. In some embodiments, the anti-cancer therapy is tumor resection or excision. In some embodiments, the anti-cancer therapy is immunotherapy.

In some embodiments, the method comprises administering the compound of Formula (I), or a pharmaceutically acceptable salt or solvate thereof (e.g., a compound of Formula (Ia)), to a patient who has failed at least one EGFR therapy (epidermal growth factor). In some embodiments, the method comprises administering the compound of Formula (I), or a pharmaceutically acceptable salt or solvate thereof, to a patient who has failed at least one EGFR TKI therapy (epidermal growth factor tyrosine kinase inhibitor).

In some embodiments, the cancer is refractory. In some embodiments, the cancer is resistant to at least one anti-cancer agent.

Methods of Dosing and Treatment Regimens

The compound of Formula (I), or a pharmaceutically acceptable salt or solvate thereof (e.g., a compound of Formula (Ia)) are used in the preparation of medicaments for the treatment of cancers.

In certain therapeutic applications, the compound of Formula (I), or a pharmaceutically acceptable salt or solvate thereof is administered to a patient already suffering from a cancer, in an amount sufficient to cure or at least partially arrest at least one of the symptoms of the cancer, for example, to reduce tumor size. Amounts effective for this use depends on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In some embodiments, the method comprises administering a compound of Formula (I), or a pharmaceutically acceptable salt or solvate thereof, to the patient orally or by intraperitoneal methods (i.p.) or a combination thereof. In some embodiments, the compound of Formula (I) is administered orally. In some embodiments, the compound of Formula (I) is administered by intraperitoneally (i.p.). In some embodiments, the compound of Formula (I) is administered directly to the tumor. In some embodiments, the compound of Formula (I) is administered intravenously (I.V.).

Doses employed for adult human treatment are typically in the range of 0.01 mg-5000 mg per day or from about 0.01 mg to about 1000 mg per day. In some embodiments, the desired dose is conveniently presented in a single dose or in divided doses. In some embodiments, the dose is provided as a single dose. In some embodiments, the dose is split into multiple doses per day.

In some embodiments, the method comprises administering the compound of Formula (I), or a pharmaceutically acceptable salt or solvate thereof to the patient daily, weekly, or monthly. In some embodiments, the compound of Formula (I) is administered daily. In some embodiments, the compound of Formula (I) is administered weekly. In some embodiments, the compound of Formula (I) is administered bi-weekly. In some embodiments, the compound of Formula (I) is administered monthly. In some embodiments, the compound of Formula (I) is administered bi-monthly.

The compound of Formula (I), or a pharmaceutically acceptable salt or solvate thereof (e.g., a compound of Formula (Ia)), can be administered, for example, once a day (QD), twice daily (BID), once a week (QW), twice weekly (BID), three times a week (TIW), or monthly (QM). In some embodiments, the method comprises administering the compound of Formula (I), or a pharmaceutically acceptable salt or solvate thereof QD, BID, or TID. In some embodiments, the compound of Formula (I) is administered QD. In some embodiments, the compound of Formula (I) is administered BID. In some embodiments, the compound of Formula (I) is administered TID. In certain instances, the compound of Formula (I) is administered 2 to 3 times a week.

In some embodiments, the compound of Formula (I) is administered QD for about 1 day to about 7 days, 1 day to about 14 days, 1 day to about 21 days, 1 day to about 28 days, or daily until disease progression or unacceptable toxicity. In some embodiments, the compound of Formula (I) is administered to the patient in need of treatment for about 7 days, 14 days, or 21 days. The administration of a compound of Formula (I) can, in part, depend upon the tolerance of the patient where greater tolerance can allow greater or more frequent administration.

In certain embodiments, the dose of the compound of Formula (I), or a pharmaceutically acceptable salt or solvate thereof being administered may be temporarily reduced or temporarily suspended for a certain length of time (i.e., a "drug holiday").

The compound of Formula (I), or a pharmaceutically acceptable salt or solvate thereof can be administered in a regimen. The regimen can be structured to provide therapeutically effective amounts of a compound of Formula (I) over a predetermined period of time (e.g., an administration time). The regimen can be structured to limit or prevent side-effects or undesired complications of the compound of Formula (I). Regimens useful for treating cancer can include any number of days of administration which can be repeated as necessary. Administration periods can be broken by a rest period that includes no administration of at least one therapy. For example, a regimen can include administration periods that include 2, 3, 5, 7, 10, 15, 21, 28, or more days. These periods can be repeated. For example, a regimen can include a set number of days as previously described where the regimen is repeated 1, 2, 3, 4, 5, 6, 7, 8, 9, 10, 11, 12, 13, or more times.

Regimens can include a rest period of at least 1, 2, 3, 5, 7, 10, or more days. The rest period can be determined by, for example, monitoring the reaction of the patient to the drug or by measuring the efficacy of the treatment. Rest periods can be applied to all of the therapies administered to the subject such that the subject receives no therapy for a set period of time during the rest period.

Regimens described herein for the treatment of cancer using the compound of Formula (I), or a pharmaceutically acceptable salt or solvate thereof, can be continued until disease progression or unacceptable toxicity. In some embodiments, the treatment is continued until disease progression is diminished or reversed (i.e., disease progression form Stage I to Stage II cancer is slowed or reversed). In some embodiments, the treatment is continued until unacceptable toxicity in the patient being treated.

Biomarkers

In another aspect, presented herein is a method of modulating one or more biomarkers over baseline levels prior to treatment in a patient in need thereof, comprising administering to the patient a SHP2 inhibitor compound of Formula (I), or a pharmaceutically acceptable salt or solvate thereof, (e.g., a compound of Formula (Ia)). In some embodiments, treatment course progression is monitored by the measurement of one or more biomarkers.

In some embodiments, the one or more biomarkers includes proinflammatory cytokines or chemokines that are important in inflammation response and immune system regulation. In some embodiments, the one or more biomarkers include but are not limited to INF-7, IL-10, IL-2, IL-4, IL-5, IL-6, IL-10, IL-12p70, and KC/GRO (CXCL1). In some embodiments, the biomarker is to INF-7. In some embodiments, the biomarker is IL-13. In some embodiments, the biomarker is IL-2. In some embodiments, the biomarker is IL-4. In some embodiments, the biomarker is IL-5. In some embodiments, the biomarker is IL-6. In some embodiments, the biomarker is IL-10. In some embodiments, the biomarker is IL-12p70. In some embodiments, the biomarker is KC/GRO.

In some embodiments, the one or more biomarkers is increased or decreased over baseline levels prior to treatment. In some embodiments, the one or more biomarkers is increased over baseline levels. In some embodiments, the one or more biomarkers is decreased over baseline levels.

In some embodiments, the one or more biomarkers is increased by at least 5%, at least 10%, at least 15%, at least 20%, at least 25%, at least 30%, at least 40%, at least 50%, at least 100%, or at least 150%. In some embodiments, the one or more biomarkers is increased by at least 1.5 times, 2 times, 3 times, 4 times, 5 times, 10 times, 15 times, 20 times, or 25 times. In some embodiments, the one or more biomarkers is decreased by at least 5%, at least 10%, at least 15%, at least 20%, at least 25%, at least 30%, at least 40%, at least 50%, at least 100%, or at least 150%. In some embodiments, the one or more biomarkers is decreased by at least 1.5 times, 2 times, 3 times, 4 times, 5 times, 10 times, 15 times, 20 times, or 25 times. In some embodiments, KC/GRO is decreased by at least 5%, at least 10%, at least 15%, at least 20%, at least 25%, at least 30%, at least 40%, at least 50%, at least 100%, or at least 150%. In some embodiments, the one or more biomarkers is decreased by at least 1.5 times, 2 times, 3 times, 4 times, 5 times, 10 times, 15 times, 20 times, or 25 times.

In some embodiments, a method of treating cancer includes reduction in the expression of DUSP6 to at least 65%, more preferably to at least 58%. In a most preferred embodiment, the expression of DUSP6 is reduced to at least 48%.

In some embodiments, a method of treating cancer includes inhibition in the expression of DUSP6 up to at least 95%, more preferably by at least 98%. In a most preferred embodiment, the expression of DUSP6 is reduced by at least 99%.

In some embodiments, a method of treating cancer includes reduction in the expression of pERK to at least 80%, more preferably to at least 88%. In a most preferred embodiment, the expression of pERK is reduced to at least 95%.

In some embodiments, the expression of DUSP6 can be used as a biomarker indicative of treatment efficiency with the compound of formula (I) or a pharmaceutically effective salt thereof.

In some embodiments, the expression of pERK can be used as a biomarker indicative of treatment efficiency with the compound of formula (I) or a pharmaceutically effective salt thereof.

In some embodiments, a method of treating cancer includes monitoring the expression of DUSP6 relative to baseline expression levels. In another embodiment, a method of treating cancer includes monitoring the expression of pERK relative to baseline expression levels.

In another aspect, presented herein is a method of modulating one or more cell populations over baseline levels prior to treatment in a patient in need thereof, comprising administering to the patient a SHP2 inhibitor compound of Formula (I), or a pharmaceutically acceptable salt or solvate thereof, (e.g., a compound of Formula (Ia)). In some embodiments, treatment course progression is monitored by the measurement of one or more cell populations. In some embodiments, the one or more cell populations includes cell populations that are important in inflammation response and immune system regulation. In some embodiments, the one or more cell populations include but are not limited to macrophages, monocytes, granulocytes, CD3+ cells, CD4+ cells, and CD8+ cells.

In some embodiments, administration of the compound of Formula (Ia) results in a reduction of macrophage populations by about 5% to about 60%. In some embodiments, administration of the compound of Formula (Ia) results in a reduction of macrophage populations by about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60%, or about 55% to about 60%. In some embodiments, administration of the compound of Formula (Ia) results in a reduction of macrophage populations by about 5%, about 10%, about 15%, about 20%, about 25%, about 30%, about 35%, about 40%, about 45%, about 50%, about 55%, or about 60%. In some embodiments, administration of the compound of Formula (Ia) results in a reduction of macrophage populations by at least about 5%, about 10%, about 15%, about 20%, about 25%, about 30%, about 35%, about 40%, about 45%, about 50%, or about 55%. In some embodiments, administration of the compound of Formula (Ia) results in a reduction of macrophage populations by at most about 10%, about 15%, about 20%, about 25%, about 30%, about 35%, about 40%, about 45%, about 50%, about 55%, or about 60%.

In some embodiments, administration of the compound of Formula (Ia) results in an increase of monocyte populations by about 5% to about 60%. In some embodiments, administration of the compound of Formula (Ia) results in an increase of monocyte populations by about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60%, or about 55% to about 60%. In some embodiments, administration of the compound of Formula (Ia) results in an increase of monocyte populations by about 5%, about 10%, about 15%, about 20%, about 25%, about 30%, about 35%, about 40%, about 45%, about 50%, about 55%, or about 60%. In some embodiments, administration of the compound of Formula (Ia) results in an increase of monocyte populations by at least about 5%, about 10%, about 15%, about 20%, about 25%, about 30%, about 35%, about 40%, about 45%, about 50%, or about 55%. In some embodiments, administration of the compound of Formula (Ia) results in an increase of monocyte populations by at most about 10%, about 15%, about 20%, about 25%, about 30%, about 35%, about 40%, about 45%, about 50%, about 55%, or about 60%.

In some embodiments, administration of the compound of Formula (Ia) results in an increase of granulocyte populations by about 5% to about 60%. In some embodiments, administration of the compound of Formula (Ia) results in an increase of granulocyte populations by about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60%, or about 55% to about 60%. In some embodiments, administration of the compound of Formula (Ia) results in an increase of granulocyte populations by about 5%, about 10%, about 15%, about 20%, about 25%, about 30%, about 35%, about 40%, about 45%, about 50%, about 55%, or about 60%. In some embodiments, administration of the compound of Formula (Ia) results in an increase of granulocyte populations by at least about 5%, about 10%, about 15%, about 20%, about 25%, about 30%, about 35%, about 40%, about 45%, about 50%, or about 55%. In some embodiments, administration of the compound of Formula (Ia) results in an increase of granulocyte populations by at most about 10%, about 15%, about 20%, about 25%, about 30%, about 35%, about 40%, about 45%, about 50%, about 55%, or about 60%.

In some embodiments, administration of the compound of Formula (Ia) results in an increase of CD3+ cell populations by about 5% to about 60%. In some embodiments, administration of the compound of Formula (Ia) results in an increase of CD3+ cell populations by about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60%, or about 55% to about 60%. In some embodiments, administration of the compound of Formula (Ia) results in an increase of CD3+ cell populations by about 5%, about 10%, about 15%, about 20%, about 25%, about 30%, about 35%, about 40%, about 45%, about 50%, about 55%, or about 60%. In some embodiments, administration of the compound of Formula (Ia) results in an increase of CD3+ cell populations by at least about 5%, about 10%, about 15%, about 20%, about 25%, about 30%, about 35%, about 40%, about 45%, about 50%, or about 55%. In some embodiments, administration of the compound of Formula (Ia) results in an increase of CD3+ cell populations by at most about 10%, about 15%, about 20%, about 25%, about 30%, about 35%, about 40%, about 45%, about 50%, about 55%, or about 60%.

In some embodiments, administration of the compound of Formula (Ia) results in an increase of CD4+ cell populations by about 5% to about 60%. In some embodiments, administration of the compound of Formula (Ia) results in an increase of CD4+ cell populations by about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60%, or about 55% to about 60%. In some embodiments, administration of the compound of Formula (Ia) results in an increase of CD4+ cell populations by about 5%, about 10%, about 15%, about 20%, about 25%, about 30%, about 35%, about 40%, about 45%, about 50%, about 55%, or about 60%. In some embodiments, administration of the compound of Formula (Ia) results in an increase of CD4+ cell populations by at least about 5%, about 10%, about 15%, about 20%, about 25%, about 30%, about 35%, about 40%, about 45%, about 50%, or about 55%. In some embodiments, administration of the compound of Formula (Ia) results in an increase of CD4+ cell populations by at most about 10%, about 15%, about 20%, about 25%, about 30%, about 35%, about 40%, about 45%, about 50%, about 55%, or about 60%.

In some embodiments, administration of the compound of Formula (Ia) results in an increase of CD8+ cell populations by about 5% to about 60%. In some embodiments, administration of the compound of Formula (Ia) results in an increase of CD8+ cell populations by about 5% to about 10%, about 5% to about 15%, about 5% to about 20%, about 5% to about 25%, about 5% to about 30%, about 5% to about 35%, about 5% to about 40%, about 5% to about 45%, about 5% to about 50%, about 5% to about 55%, about 5% to about 60%, about 10% to about 15%, about 10% to about 20%, about 10% to about 25%, about 10% to about 30%, about 10% to about 35%, about 10% to about 40%, about 10% to about 45%, about 10% to about 50%, about 10% to about 55%, about 10% to about 60%, about 15% to about 20%, about 15% to about 25%, about 15% to about 30%, about 15% to about 35%, about 15% to about 40%, about 15% to about 45%, about 15% to about 50%, about 15% to about 55%, about 15% to about 60%, about 20% to about 25%, about 20% to about 30%, about 20% to about 35%, about 20% to about 40%, about 20% to about 45%, about 20% to about 50%, about 20% to about 55%, about 20% to about 60%, about 25% to about 30%, about 25% to about 35%, about 25% to about 40%, about 25% to about 45%, about 25% to about 50%, about 25% to about 55%, about 25% to about 60%, about 30% to about 35%, about 30% to about 40%, about 30% to about 45%, about 30% to about 50%, about 30% to about 55%, about 30% to about 60%, about 35% to about 40%, about 35% to about 45%, about 35% to about 50%, about 35% to about 55%, about 35% to about 60%, about 40% to about 45%, about 40% to about 50%, about 40% to about 55%, about 40% to about 60%, about 45% to about 50%, about 45% to about 55%, about 45% to about 60%, about 50% to about 55%, about 50% to about 60%, or about 55% to about 60%. In some embodiments, administration of the compound of Formula (Ia) results in an increase of CD8+ cell populations by about 5%, about 10%, about 15%, about 20%, about 25%, about 30%, about 35%, about 40%, about 45%, about 50%, about 55%, or about 60%. In some embodiments, administration of the compound of Formula (Ia) results in an increase of CD8+ cell populations by at least about 5%, about 10%, about 15%, about 20%, about 25%, about 30%, about 35%, about 40%, about 45%, about 50%, or about 55%. In some embodiments, administration of the compound of Formula (Ia) results in an increase of CD8+ cell populations by at most about 10%, about 15%, about 20%, about 25%, about 30%, about 35%, about 40%, about 45%, about 50%, about 55%, or about 60%.

Definitions

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, headings provided herein are for convenience only and do not interpret the scope or meaning of the claimed invention.

The terms below, as used herein, have the following meanings, unless indicated otherwise:

"Oxo" refers to the =O substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_5$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_5$ alkyl, $C_3$-$C_5$ alkyl and $C_4$-$C_5$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl or ethyl. Preferably, the $C_1$-$C_{10}$ alkyl is any one of methyl, ethyl, n-propyl, isopropyl, and tert-butyl. Unless stated otherwise specifically in the specification, an alkyl group may be optionally substituted as described below.

"Alkylene" refers to a straight or branched divalent hydrocarbon chain linking the rest of the molecule to a radical group. In some embodiments, the alkylene is —CH$_2$—, —CH$_2$CH$_2$—, or —CH$_2$CH$_2$CH$_2$—. In some embodiments, the alkylene is —CH$_2$—. In some embodiments, the alkylene is —CH$_2$CH$_2$—. In some embodiments, the alkylene is —CH$_2$CH$_2$CH$_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy. The term "$C_1$-$C_{10}$ alkoxy" alone or in combination means the group $C_1$-$C_{10}$ alkyl-O—, wherein "$C_1$-$C_{10}$ alkyl" means as defined above, which includes, but not limited to, methoxy (—OCH$_3$), ethoxy (—OCH$_2$CH$_3$), n-propoxy (—OCH$_2$CH$_2$CH$_3$), iso-propoxy (—OCH(CH$_3$)$_2$), n-butoxy (—OCH$_2$CH$_2$CH$_2$CH$_3$), sec-butoxy (—OCH(CH$_3$)CH$_2$CH$_3$), iso-butoxy (—OCH$_2$CH(CH$_3$)$_2$), tert-butoxy (—OC(CH$_3$)$_3$), etc.

"Heteroalkyl" refers to an alkyl radical as described above where one or more carbon atoms of the alkyl is replaced with a O, N (i.e., NH, N-alkyl) or S atom. "Heteroalkylene" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —OCH$_2$OMe, —OCH$_2$CH$_2$OMe, or —OCH$_2$CH$_2$OCH$_2$CH$_2$NH$_2$. Representative heteroalkylene groups include, but are not limited to, —OCH$_2$CH$_2$O—, —OCH$_2$CH$_2$OCH$_2$CH$_2$O—, or —OCH$_2$CH$_2$OCH$_2$CH$_2$OCH$_2$CH$_2$O—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —CO$_2$H. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

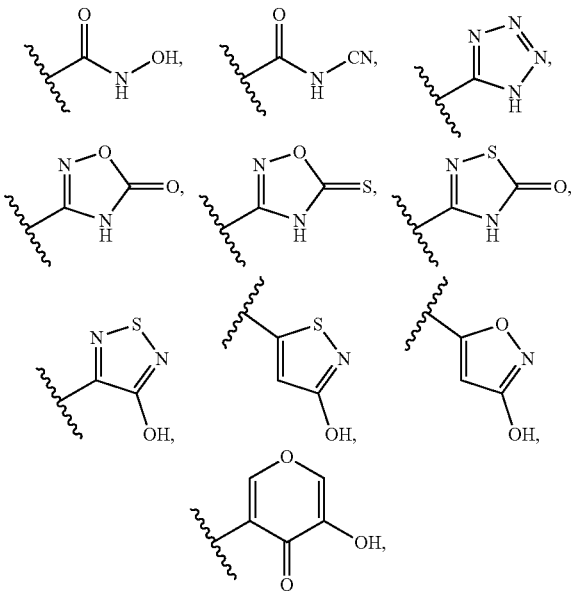

and the like.

"Cycloalkyl" refers to a monocyclic or polycyclic non-aromatic radical, wherein each of the atoms forming the ring (i.e., skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloalkyls having from three to ten carbon atoms, from three to eight carbon atoms, from three to six carbon atoms, or from three to five carbon atoms. In some embodiments, a cycloalkyl is a $C_3$-$C_6$ cycloalkyl. In some embodiments, the cycloalkyl is monocyclic, bicyclic or polycyclic. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, bicyclo[1.1.1]pentyl, bicyclo[3.3.0]octane, bicyclo[4.3.0]nonane, bicyclo[2.1.1]hexane, bicyclo[2.2.1]heptane, bicyclo[2.2.2]octane, bicyclo[3.2.2]nonane, bicyclo[3.3.2]decane, norbornyl, decalinyl and adamantyl. In some embodiments, the cycloalkyl is monocyclic. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. In some embodiments, the cycloalkyl is bicyclic. Bicyclic cycloalkyl groups include fused bicyclic cycloalkyl groups, spiro bicyclic cycloalkyl groups, and bridged bicyclic cycloalkyl groups. In some embodiments, cycloalkyl groups are selected from among spiro[2.2]pentyl, bicyclo[1.1.1]pentyl, bicyclo[3.3.0]octane, bicyclo[4.3.0]nonane, bicyclo[2.1.1]hexane, bicyclo[2.2.1]heptane, bicyclo[2.2.2]octane, bicyclo[3.2.2]nonane, bicyclo[3.3.2]decane, norbornyl, 3,4-dihydronaphthalen-1(2H)-one and decalinyl. In some embodiments, the cycloalkyl is polycyclic. Polycyclic radicals include, for example, adamantyl, and. In some embodiments, the polycyclic cycloalkyl is adamantyl. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoethoxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 10 carbon atoms and from one to 4 heteroatoms selected from the group consisting of nitrogen, oxygen, and sulfur. Unless stated otherwise specifically in the specification, the heterocycloalkyl radical may be a monocyclic, bicyclic ring (which may include a fused bicyclic heterocycloalkyl (when fused with an aryl or a heteroaryl ring, the heterocycloalkyl is bonded through a non-aromatic ring atom), bridged heterocycloalkyl or spiro heterocycloalkyl), or polycyclic. In some embodiments, the heterocycloalkyl is monocyclic or bicyclic. In some embodiments, the heterocycloalkyl is monocyclic. In some embodiments, the heterocycloalkyl is bicyclic. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. In some embodiments, heterocycloalkyls have from 2 to 10 carbons, 0-2 N atoms, 0-2 O atoms, and 0-1 S atoms in the ring. In some embodiments, heterocycloalkyls have from 2 to 10 carbons, 1-2 N atoms, 0-1 O atoms, and 0-1 S atoms in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, a heterocycloalkyl group may be optionally substituted. In some embodiments, the term "3-12 membered heterocyclic group" refers to a saturated or partially unsaturated monocyclic ring containing 3-12, particularly 5-12, more particularly 5-7 carbon atoms and heteroatoms or heteroatom groups or a polycyclic heterocyclic group, the heteroatom or heteroatom group is selected from N, NH, O, C(O), S(O)$_m$ (where m is 0, 1 or 2). In some embodiments, the 3-12 membered heterocyclic groups include aziridinyl, azetidinyl, oxetanyl, pyrrolidinyl, tetrahydrofuranyl, tetrahydrothienyl, piperidinyl, morpholinyl, piperazinyl, thiomorpholine, tetrahydropyranyl, 1,1-dioxothiomorpholinyl, butyrolactamyl, valerolactam, caprolactam, butyrolactone, valerolactone, or caprolactone.

"Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, pyrazinyl, pyrimidinyl, thiazolyl, thienyl, thiadiazolyl or furyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, a bicyclic heteroaryl is a $C_6$-$C_9$ heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$ alkylalkyne, halogen, acyl, acyloxy, —$CO_2$H, —$CO_2$ alkyl, nitro, and amino, including mono- and di-substituted amino groups (e.g., —$NH_2$, —NHR, —$NR_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2$H, and —$CO_2$ alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (=O).

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

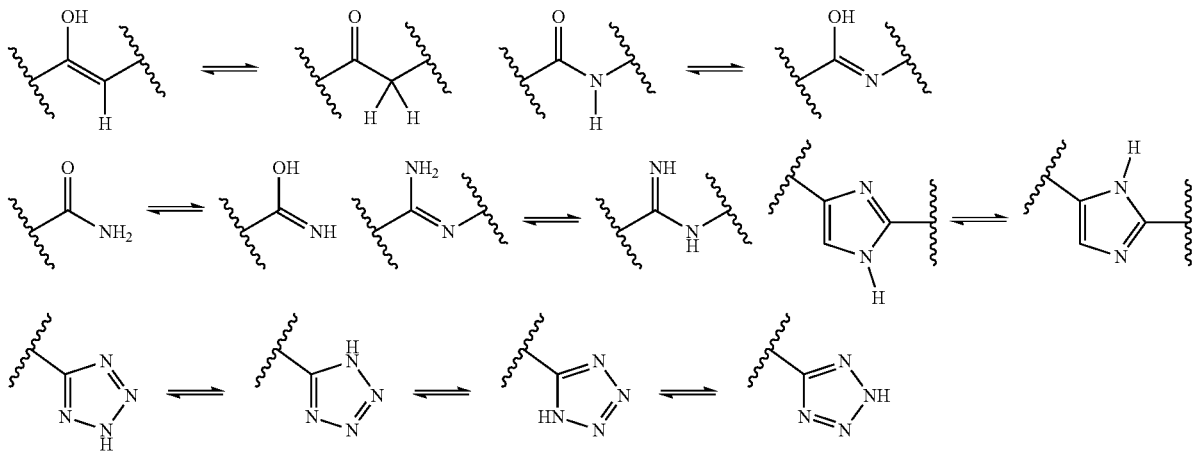

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "pharmaceutical combination" as used herein, means a product that results from the mixing or combining of more than one active ingredient and includes both fixed and non-fixed combinations of the active ingredients. The term "fixed combination" means that the active ingredients, e.g., a compound of Formula (I) and a co-agent, are both administered to a patient simultaneously in the form of a single entity or dosage. The term "non-fixed combination" means that the active ingredients, e.g., a compound of Formula (I) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "cancer" refers to any physiological condition in mammals characterized by unregulated cell growth. Cancers described herein include solid tumors and hematological (blood) cancers. A "hematological cancer" refers to any blood borne cancer and includes, for example, myelomas, lymphomas and leukemias. A "solid tumor" or "tumor" refers to a lesion and neoplastic cell growth and proliferation, whether malignant or benign, and all pre-cancerous and cancerous cells and tissues resulting in abnormal tissue growth. "Neoplastic," as used herein, refers to any form of dysregulated or unregulated cell growth, whether malignant or benign, resulting in abnormal tissue growth.

The term "enhance" refers to an increase or improvement in the function or activity of a protein or cell after administration or contacting with a combination described herein compared to the protein or cell prior to such administration or contact.

The term "anti-cancer agent" is used in accordance with its plain ordinary meaning and refers to a composition having anti-neoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The term "chemotherapeutic" or "chemotherapeutic agent" is used in accordance with its plain ordinary meaning and refers to a chemical composition or compound having anti-neoplastic properties or the ability to inhibit the growth or proliferation of cells. "Chemotherapy" refers to a therapy or regimen that includes administration of a chemotherapeutic or anti-cancer agent described herein.

The terms "polypeptide" and "protein" are used interchangeably herein and refer to any molecule that includes at least 2 or more amino acids.

The term "regimen" refers to a protocol for dosing and timing the administration of one or more therapies (e.g., combinations described herein or another active agent such as for example an anti-cancer agent described herein) for treating a disease, disorder, or condition described herein. A regimen can include periods of active administration and periods of rest as known in the art.

EXAMPLES

It will be appreciated that the following examples are intended to illustrate but not to limit the present disclosure. Various other examples and modifications of the foregoing description and examples will be apparent to a person skilled in the art after reading the disclosure without departing from the spirit and scope of the disclosure, and it is intended that all such examples or modifications be included within the scope of the appended claims. All publications and patents referenced herein are hereby incorporated by reference in their entirety.

Example 1 Synthesis of Compound of Formula (Ia)

The compounds of Formula (I), (Ia), and (II), can be synthesized by the methods provided in PCT/CN2020/07791, which is herein incorporated by reference in its entirety. In some embodiments, the synthesis of compounds described herein are accomplished using means described in the chemical literature, using the methods described herein, or by a combination thereof.

Example 2: Materials and Methods

Reagents: GH21001 (TNO-155), GH21005 (HBI-2376) were supplied by HUYA Biosciences, USA, RMC-4550 was purchased from MCE, China. Osimertinib was purchased from Selleck, China. Cisplatin was purchased from Qilu Pharma, China. Anti-PD-1 (RMP1-14) and Rat IgG2a antibodies were purchased from BioXCell (China).

Cell lines and maintenance: All cell lines used for in vitro and in vivo studies were supplied as part of Crown Biosciences cell bank except KYSE520, which was provided by HUYABIO. All cell lines were maintained according to source at 37° C. and 5% $CO_2$ unless otherwise noted. Human Lung cancer cell lines NCI-H358, HCC827, Esophageal cancer cell line KYSE520, Stomach cancer cell line NCI-N87 and Mouse Colon cancer cell line MC38 were cultured in RPMI1640+10% FBS. Pancreatic cell line MiaPaca-2 was cultured in MDME+10% FBS+2.5% HS. Pancreatic cancer cell line CAPAN-1 was cultured in IMDM+20% FBS. Brain cancer cell line U87MG was cultured in MEM+

0.01 mM NEAA+10% FBS. Lung cancer cell line HCC827-ER1 (Derived from HCC827 at Crown Biosciences) was cultured in RPMI1640+10% FBS+42 μM erlotinib. Lung cancer cell line NCI-H1975 (developed at Synthego Corporation) was cultured in RPMI1640+10% FBS+100 μg/ml Hygromycin (Sun, 2020).

Figure 9A:
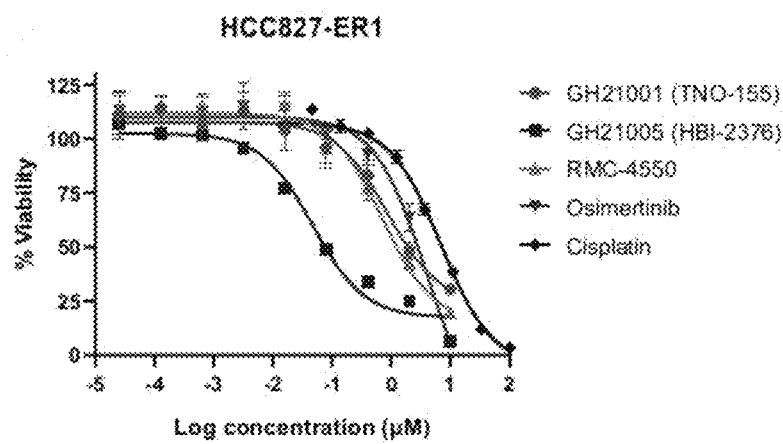
FIG. 9A shows that the compound of Formula (Ia) reduces viability of lung cancer cell line HCC827-ER1.
Figure 9B:
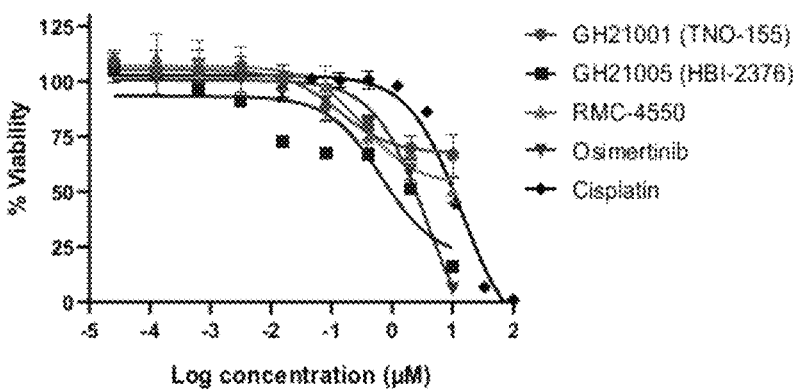
FIG. 9B shows the compound of Formula (Ia) reduces viability of Osimertinib resistant cancer cell line NCI-H1975 (L858R/T790M/C797S).

Cell Viability Assay: For cell cytotoxicity assays, cells were plated in 96-well plates and plating densities were determined on the basis of Crown Biosciences Cell line Database. Cells were plated at 2000 cells/well. Twenty four hours after plating, cells were treated with inhibitors at the indicated compound concentrations. On Day 5, cells were lysed with CellTiter-Glo® Luminescent Cell Viability Assay reagent (Promega) and luminescence was read using the EnVision Multi-plate reader. To calculate $IC_{50}$ values, a dose-response curve is generated using a nonlinear regression model with a sigmoidal dose response. The formula of surviving rate is shown below. $IC_{50}$ values were automatically generated by GraphPad Prism 8.0. The results of these assays are depicted in FIG. 1 and Table 1, and further in FIG. 9A (HCC827-ER1) and 9B (NCI-H1975 (L858R/T790M/C797S)).

TABLE 1

| Compound Cell line | GH21001 | GH21005 | RMC-4550 | Cisplatin |
|---|---|---|---|---|
| NCI-H358 | 0.46 | 0.03 | 0.44 | 4.85 |
| NCI-H1975 | NA | 0.21 | 1.44 | 3.99 |
| MIAPaCa-2 | NA | NA | NA | 7.15 |
| U87MG | 1.53 | 0.23 | 3.9 | 1.58 |
| Capan-1 | 6.06 | NA | NA | 0.27 |
| KYSE 520 | 0.45 | 0.06 | 0.49 | 6.8 |
| NCI-N87 | 0.23 | 0.01 | 0.26 | 2.35 |
| HCC827 | 0.41 | 0.02 | 0.69 | 4.79 |

Values are in uM

Example 3: Animal Models and In Vivo Treatments

Procedures involving the care and use of animals in this study were reviewed and approved by the Institutional Animal Care and Use Committee (IACUC) of Crown Biosciences prior to execution. During the study, the care and use of animals were conducted in accordance with the regulations of the Association for Assessment and Accreditation of Laboratory Animal Care (AAALAC). Animals (6-8 weeks) were obtained from Shanghai Lingchang Biotechnology Co., Ltd (Shanghai, China) and were allowed to acclimate prior to tumor cell inoculation.

All cell lines were maintained in culture and cells in exponential growth phase were harvested and quantitated by cell counter before tumor inoculation. MC38 tumor cells ($1\times10^6$) in 0.1 ml of PBS were inoculated into the right front flank of female C57/Bl animals, mean tumor size approximately 112 mm³ at the start of treatment. NCI-H1975 (EGFR L858R/T7900M/C797S) tumor cells ($1\times10^7$) in 0.1 ml of PBS mixed with Matrigel (1:1) inoculated into female NOD/SCID animals, mean tumor approximately 200 mm³ at the start of treatment. HCC827-ER1 tumor cells ($5\times10^7$) in 0.1 ml of PBS mixed with Matrigel (1:1) inoculated into female Balb/C Nude animals, mean tumor approximately 325 mm³ at the start of treatment.

Figure 2A:
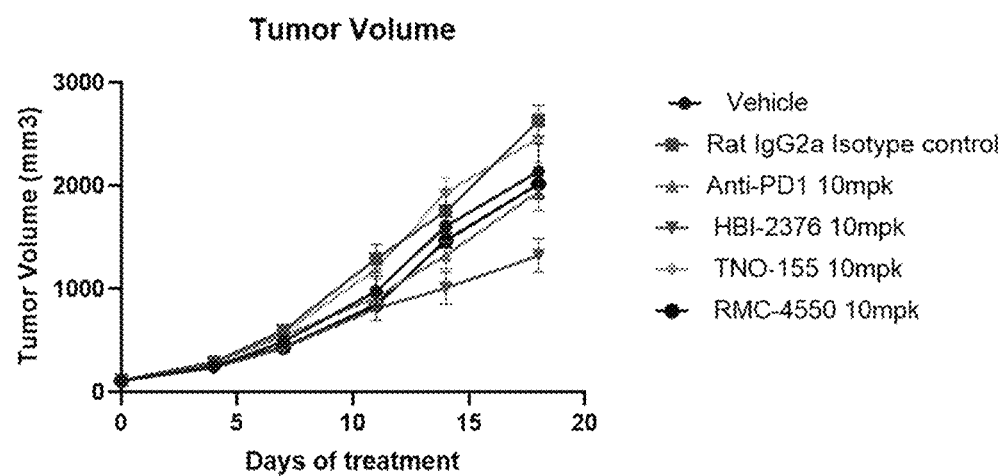
FIG. 2A-2B shows the effect of compound of Formula (Ia) on tumor volume and % change in body weight in a MC38 model.
Figure 2B:
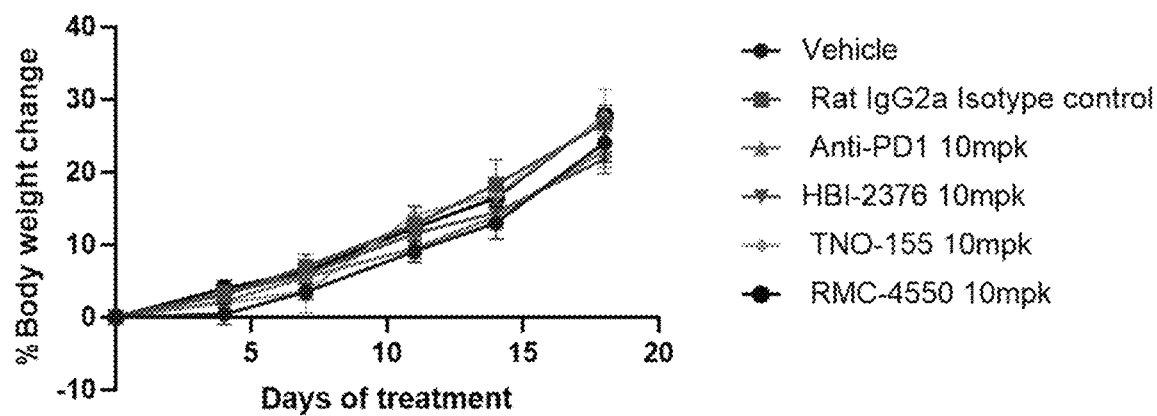
Figure 10A:
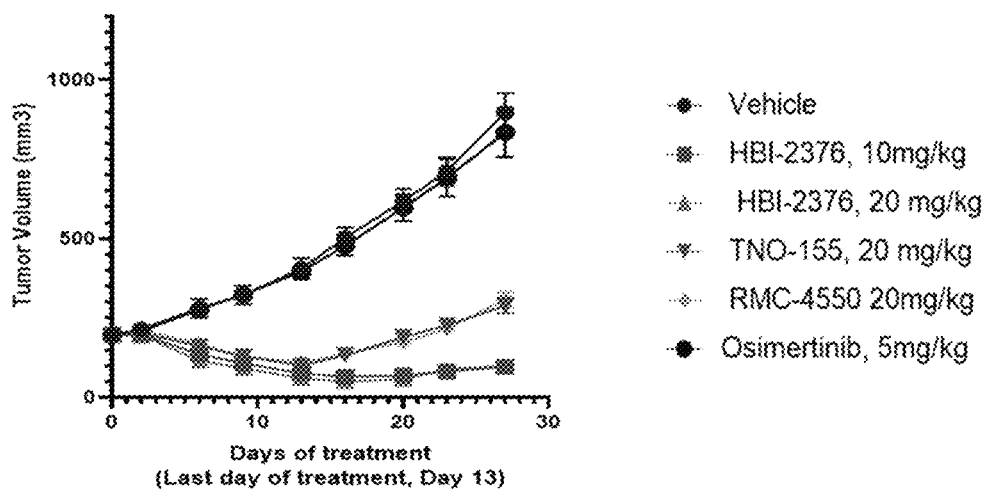
FIG. 10A-10B shows the effect of compound of Formula (Ia) on tumor volume and body weight in NCI-H1975 (L858R/T790M/C797S) Osimertinib resistant cancers.
Figure 10B:
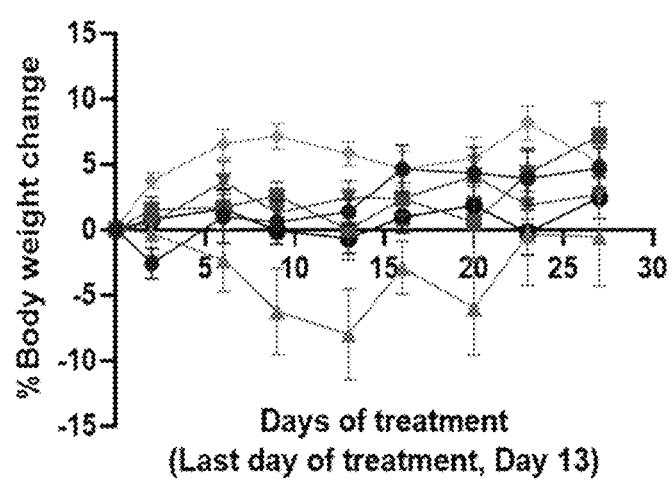
Figure 12A:
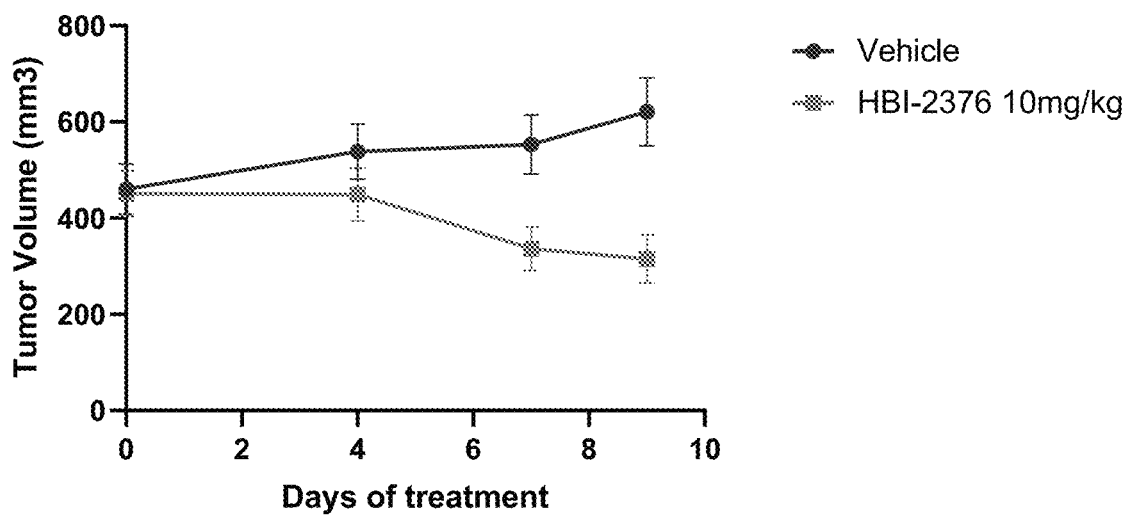
FIG. 12A-12B shows the effect of compound of Formula (Ia) on tumor volume and % change in body weight in HCC827 CDX tumor model.
Figure 12B:
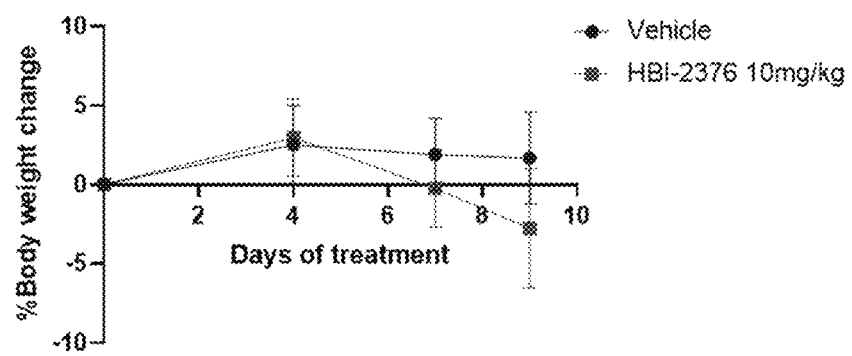

The date of randomization and treatment initiation was denoted as day 0. Tumor volumes were measured twice per week in two dimensions using a caliper, and the volume will be expressed in mm³ using the formula: V=(L×W×W)/2, where V is tumor volume, L is tumor length (the longest tumor dimension) and W is tumor width (the longest tumor dimension perpendicular to L). Dosing volume was 10 mL/kg/day. GH21001 and GH21005 were dissolved in HP-β-CD with 200 ml of 50 mM sodium citrate (pH=4.2). Anti-PD-1 and Rat IgG2a were diluted in PBS. RMC-4550 was diluted in 1% Capitsol in 50 mM sodium citrate (pH=5.0) 0.5% dosing solution of osimertinib was diluted in 2% DMSO/30% PEG300. The results of these experiments are depicted in FIG. 2A-B (MC38 tumors) and FIG. 10A-10B (NCI-H1975 (L858R/T790M/C797S) tumors). The results for HCC827 CDX model are depicted in FIG. 12A-B. Upon termination, tumors were collected. A portion of the tumor was minced and snap frozen immediately for protein isolation or tumor tissue was dissociated for FACs analysis. Another portion of the tumor was fixed in 10% neutral buffered formalin prior to processing into paraffin blocks.

Example 4: Tumor and Blood Immunotyping!

Tumor dissociation: Upon termination animals bearing MC38 tumors, tumors and blood was harvested 12 hours post last dose. Tumors were enzymatically and mechanically dissociated using The Tumor Dissociation Kit (130-096-730) Miltenyi Biotec MACS Technology. Mononuclear blood cells (PBMCs) were isolated from whole blood using Histopaque-1077 (Sigma).

Figure 3:
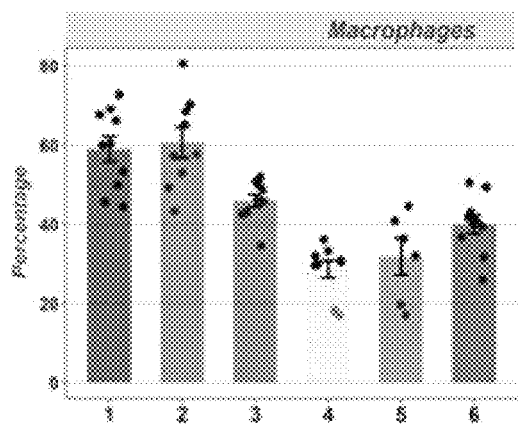
FIG. 3 shows that the compound of Formula (Ia) reduces macrophage populations in MC38 tumors.
Figure 4:
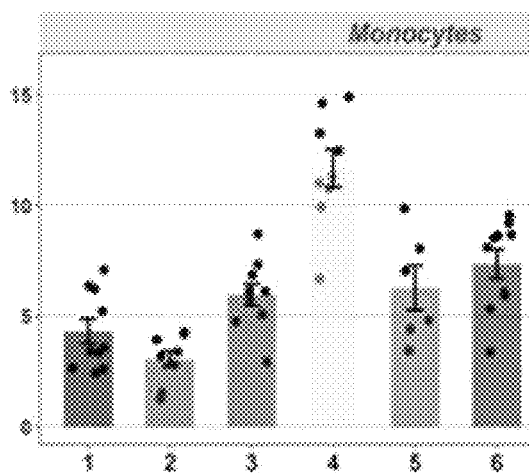
FIG. 4 shows that the compound of Formula (Ia) increases monocyte populations in MC38 tumors.
Figure 5:
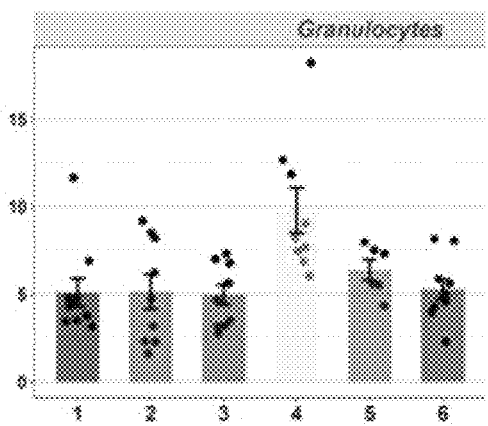
FIG. 5 shows that the compound of Formula (Ia) increases granulocyte populations in MC38 tumors.
Figure 6:
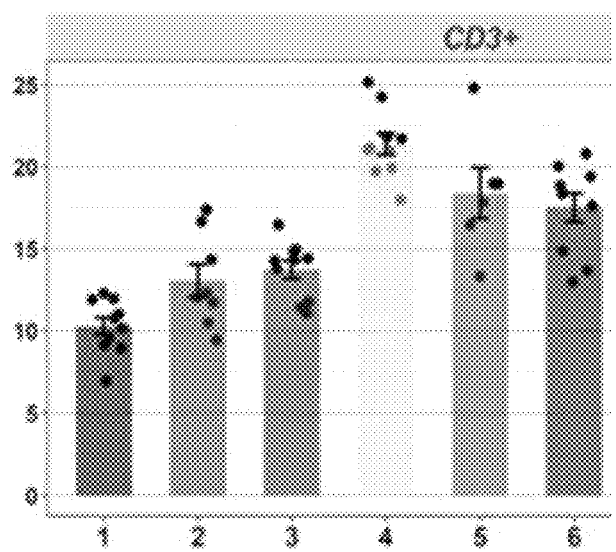
FIG. 6 shows that the compound of Formula (Ia) increases circulating CD3+ cell populations in MC38 tumors.
Figure 7:
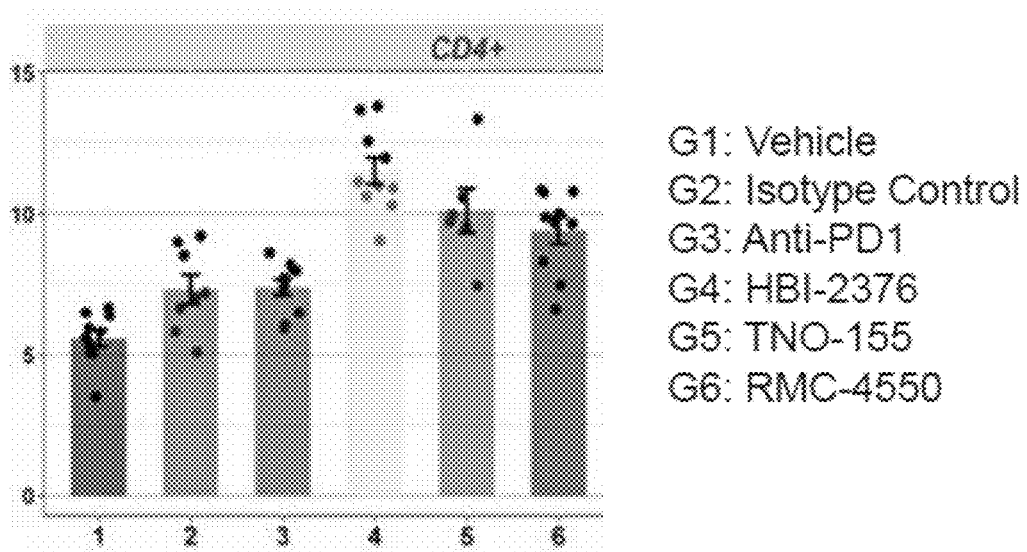
FIG. 7 shows that the compound of Formula (Ia) increases circulating CD4+ cell populations in MC38 tumors.
Figure 8:
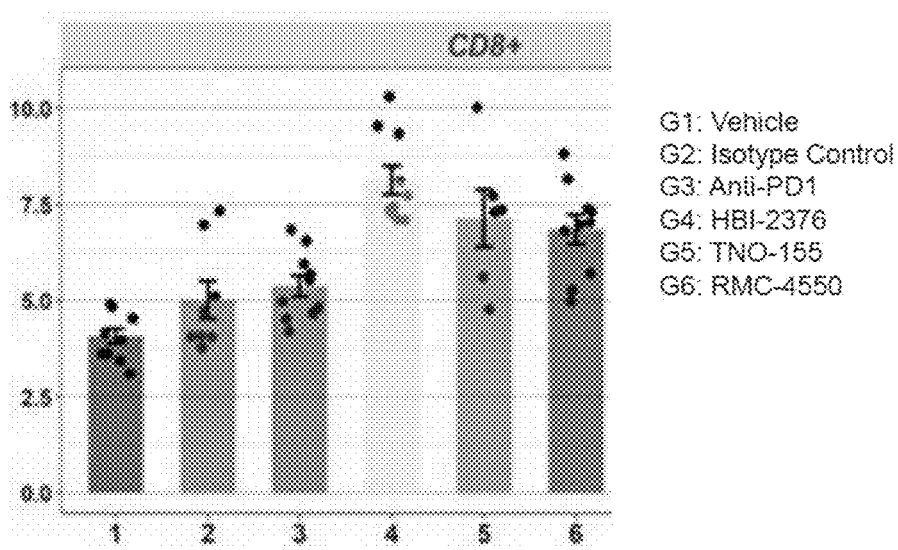
FIG. 8 shows that the compound of Formula (Ia) increases circulating CD8+ cell populations in MC38 tumors.

Tumor cell suspension, whole lysed blood or isolated PBMCs were resuspended and blocked in staining buffer with 1 μg/ml Fc-Block (Mouse BD Fc Block™ CAT #553141). All antibodies were diluted in Fc Blocking buffer except FoxP3 which was diluted in Permeabilization Buffer. Antibodies were diluted according to Crown Biosciences optimization. Cell surface markers CD45, CD4, CD335, CD11b, Gr-1 were purchased from Biolegend. CD3 was purchased from BD Biosciences. CD8, FoxP3 and LD BD were purchased from eBiosciences. Data was collected on a cytometer and data was analyzed using Kaluza Analysis Software. The results of these experiments are depicted in FIG. 3 (macrophages), FIG. 4 (monocytes), FIG. 5 (granulocytes), FIG. 6 (CD3+ cells), FIG. 7 (CD4+ cells), and FIG. 8 (CD8+ cells).

Figure 11:
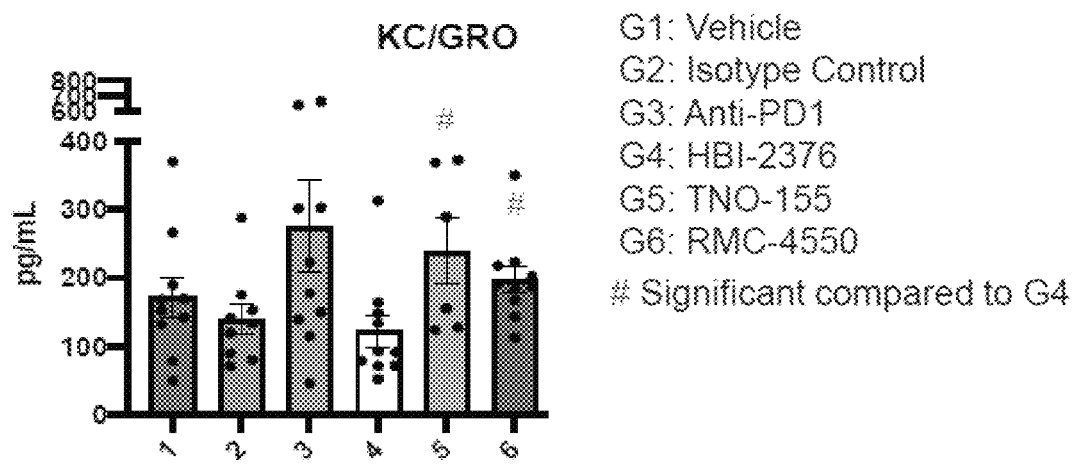
FIG. 11 shows that the compound of Formula (Ia) reduces KC/GRO significantly more than GH21001 (TNO-155) and RMC-4550.

Cytokine detection assay: V-Plex Proinflammatory Panel 1 Mouse Kit (Mesoscale Discovery) was used to determine cytokine levels in plasma isolated from tumor bearing animals 2 hours post last dose. Plasma from tumor bearing animals was analyzed as described by the manufacture's guidelines. Briefly, diluted plasma is introduced to the MSD plate pre-coated with capture antibodies to KC/GRO. After incubation, samples are washed and incubated with secondary detection antibody, (MSD SULFO-TAG™). Electrochemiluminescence detection from the assay is analyzed on the Meso Scale Discovery platform and cytokine levels calculated according to manufacturer's control samples. The results of this experiment are depicted in FIG. 11—it was observed that the compound of Formula (Ia) significantly reduced KC/GRO as compared to GH21001 (TNO-155) and RMC-4550.

Immunoblot Analysis: Tumors were harvested at the respective time point post dose and were snap frozen in liquid nitrogen. Tissue was ground in liquid nitrogen using a mortar and pestle and weighed. The volume of RIPA buffer containing phosphatase and protease inhibitors was added at 3 times the weight, samples were inverted and place on ice for 30 min. Cell lysate was obtained by centrifugation at 14,000 g for 15 min at 4° C. and supernatant was transferred to a fresh tube. Protein was quantified using Pierce BCA Protein Assay kit. 50 μg of protein was loaded in each well.

Figure 13A:
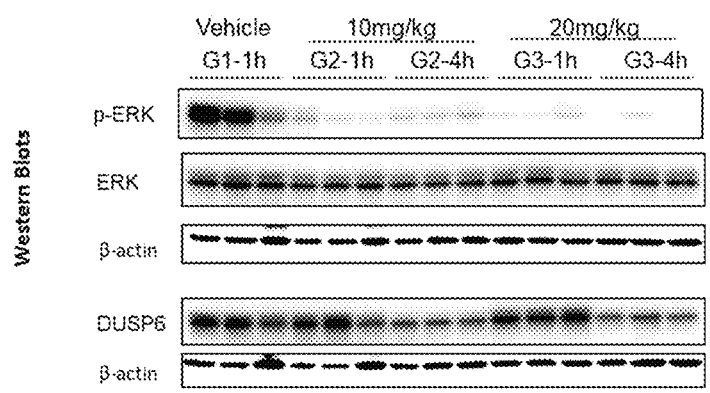
FIG. 13A-13D shows the effect of compound of Formula (Ia) on pERK and DUSP6 expression in HCC827 CDX tumor model, 14D quantifies the amount of DUSP6 gene expression.
Figure 13B:
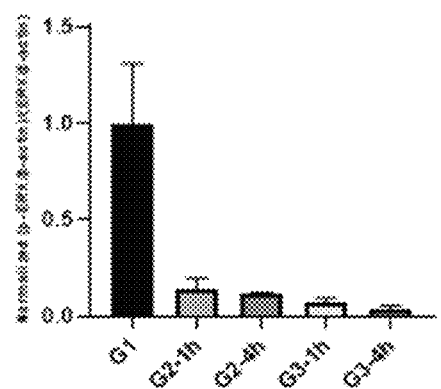
Figure 13C:
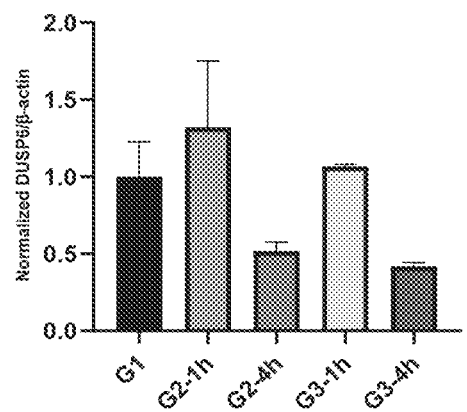
Figure 13D:
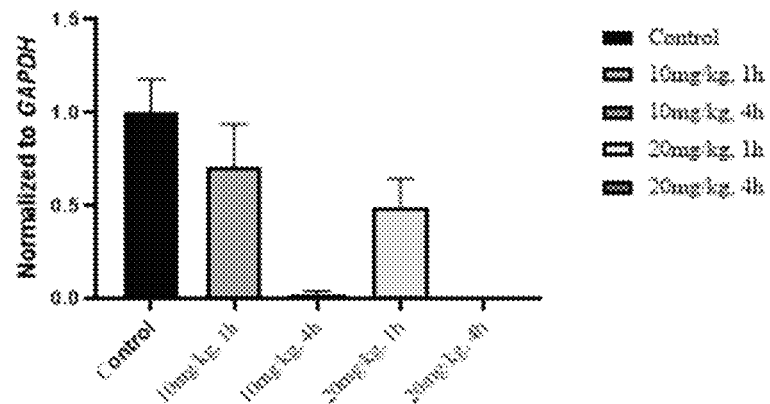
Figure 13E:
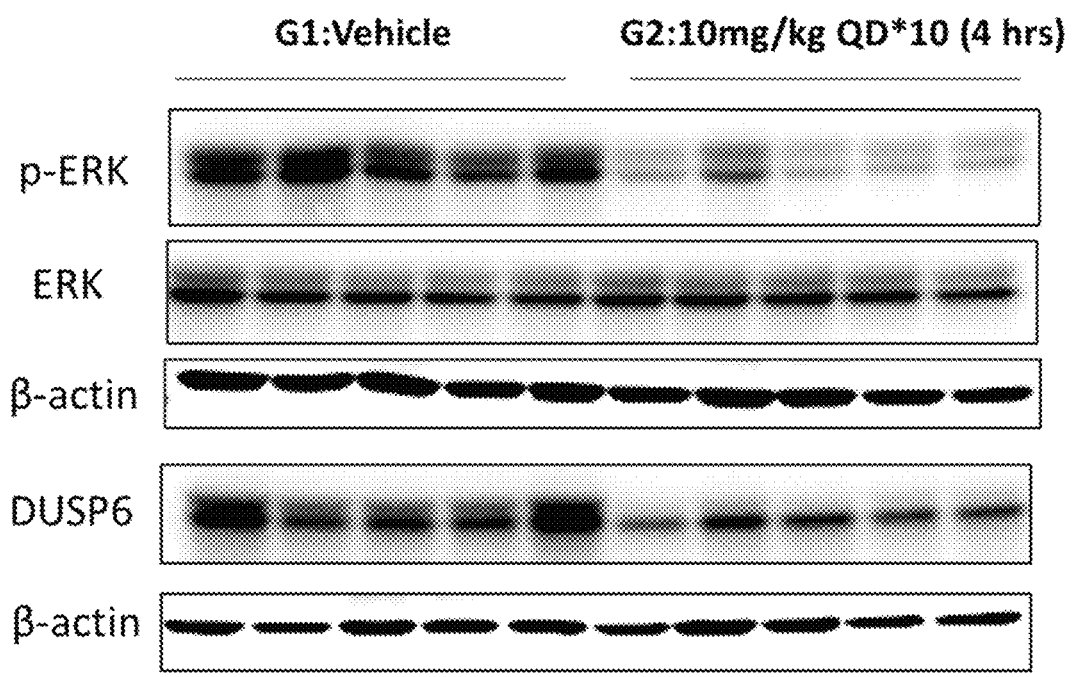
FIG. 13E-13G shows the effect of compound of Formula (Ia) on pERK and DUSP6 expression in HCC827 CDX tumor model, 14G quantifies the level of DUSP6 relative to housekeeping gene GAPDH.
Figure 13F:
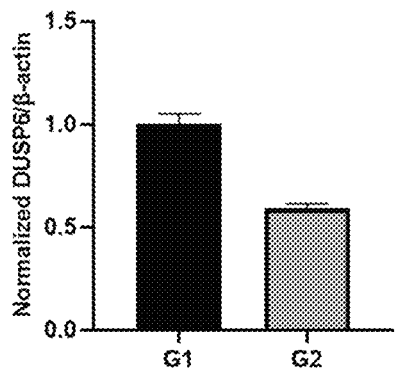
Figure 13F:
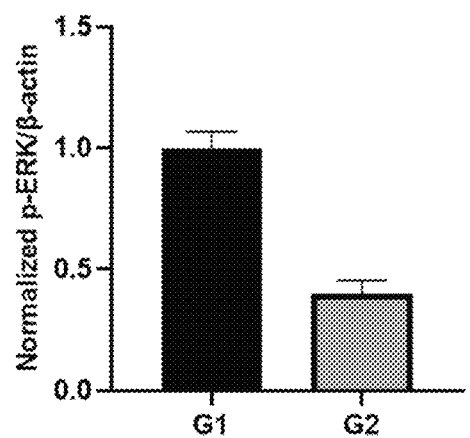
Figure 13G:
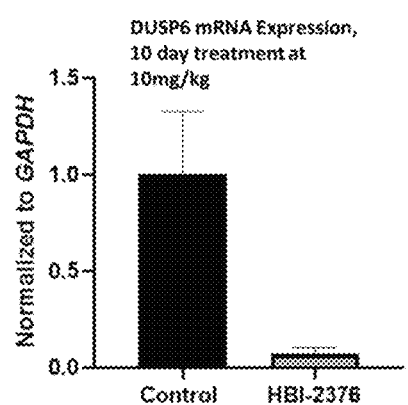
Figure 14A:
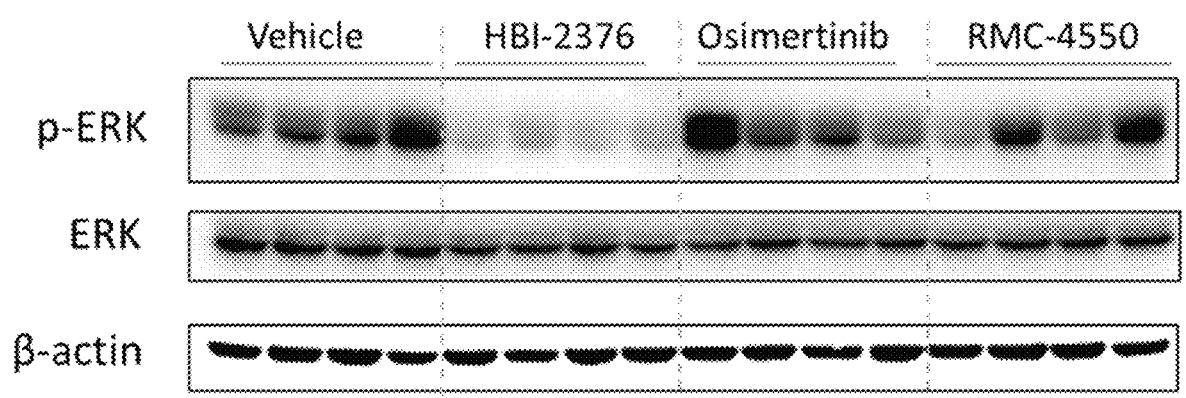
FIG. 14A shows the effect of compound of Formula (Ia) on pERK expression in HCC827-ER1 CDX tumor model.
Figure 14B:
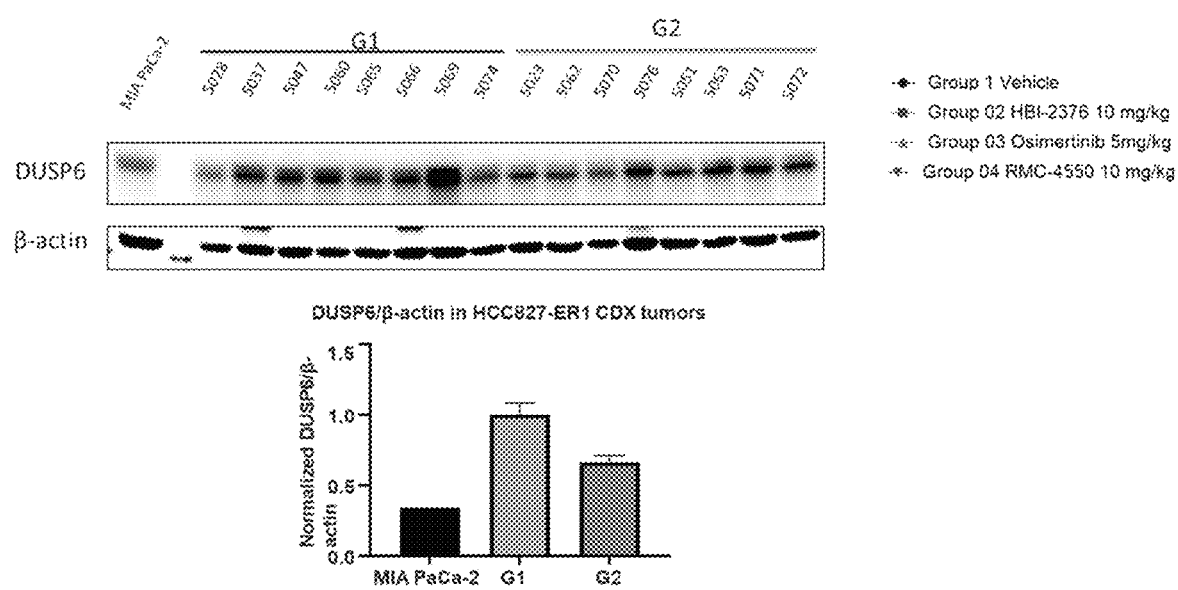
FIG. 14B shows the effect of compound of Formula (Ia) on DUSP6 expression in HCC827-ER1 CDX tumor model; it also quantifies the level of DUSP6.

Gels were transferred to preactivated PVDF and primary and secondary antibodies were diluted in TBST with 5% dry milk. Target proteins were detected with Tanon 5200 chemiluminescence image analysis system using ECL method. Primary antibodies: DUSP6, Abcam ab76310, β-actin CST 3700S, p-ERK CST 4370s, ERK CST 4695s. The results of these experiments in a HCC827 CDX xenograft model are depicted in FIG. 13A, FIG. 13B, and, FIG. 13C. Also see FIG. 13E and FIG. 13F, and in a HCC827_ER1 CDX xenograft model are depicted in FIG. 14A and FIG. 14B.

qPCR Analysis: Tumor tissue was harvested 4 hours post dose and tissue was snap frozen in liquid nitrogen. Tissue was ground in liquid nitrogen using a mortar and pestle and weighed. Tissue was placed in RLT buffer containing a stainless steel bead and placed in the TissueLyser. RNA was processed using RNAeasy mini spin kit (Qiagen 74106). Total RNA was quantified by Nanodrop™ 2000 spectrophotometer. cDNA was prepared using High Capacity cDNA Reverse Transcriptase Kit (ABI 4374966). Real time PCR was preformed using TaqMan Universal PCR Master Mix (ABI 4304437) with DUSP6 probe (Theremo Fisher 4331182) and GAPDH probe (ThermoFisher 4351370) using Applied Biosystems Inc, fact PCR system 7900H. Raw data were analyzed by SDS 2.4 and processed using the ΔCt relative quantification method. ΔCt values were calculated against the human house-keeping gene, GAPDH. ΔΔCt values were calculated against the vehicle groups. $2^{-\Delta\Delta Ct}$ represents target gene, DUSP6, expression level. The results of these experiments in a HCC827 CDX xenograft model for DUSP6 expression are depicted in FIG. 13D, FIG. 13G.

Figure 15A:
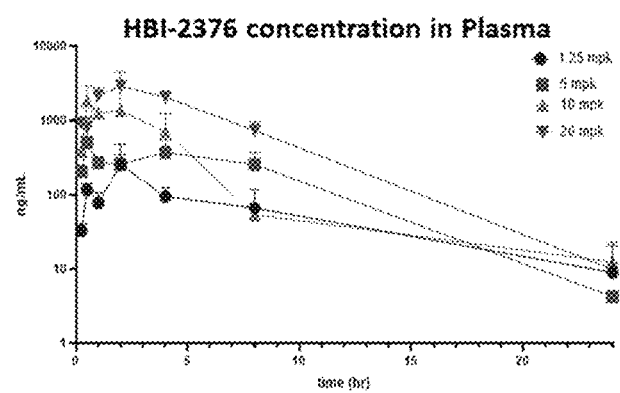
FIG. 15A monitors the amount of compound of Formula (Ia) in plasma, in a HCC827 CDX tumor model.
Figure 15B:
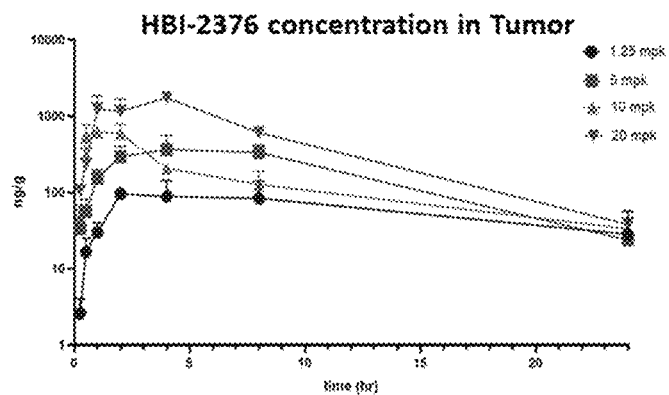
FIG. 15B monitors the amount of compound of Formula (Ia) in tumor, in a HCC827 CDX tumor model.

Pharmacokinetic Analysis: Blood and tumors were collected N=3/timepoint (plasma) or N=3/timepoint (tumor tissue) from tumor bearing animals at respective time points after a single dose of HBI-2376 at respective dose concentrations. Samples were analyzed by LC-MS/MS analysis with Phoenix WinNonlin 6.3 to determine the concentration of compound in plasma or tumor samples. Concentrations were calculated using Linear/log trapezoidal rule. The results of these experiments in a HCC827 CDX xenograft model are depicted in FIG. 15A and FIG. 15B.

It is to be understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating cancer in a patient in need thereof, said method comprising administering to said patient a therapeutically effective amount of a compound having the structure of Formula (Ia), or a pharmaceutically acceptable salt or solvate thereof:

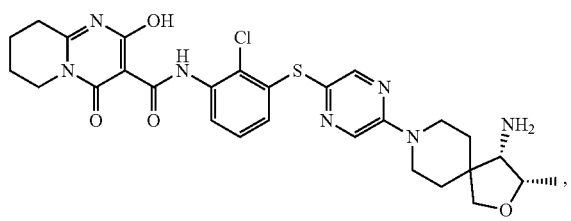 [SMILES: C[C@@H]1OCC2(CCN(c3cnc(Sc4cccc(NC(=O)c5c(O)nc6n(c5=O)CCCC6)c4Cl)cn3)CC2)[C@@H]1N]

(Ia)

wherein said cancer is non-small cell lung cancer, esophageal cancer, stomach cancer, or brain tumor; and wherein said patient has failed at least one anti-cancer agent therapy, wherein said anti-cancer agent is an EGFR TK inhibitor.

2. The method of claim 1, wherein said method comprises administering said compound to said patient as third, fourth, fifth, or sixth line of treatment.

3. The method of claim 1, wherein said compound, or a pharmaceutically acceptable salt thereof is administered to said patient in need at about 5 mg/kg, about 10 mg/kg, about 15 mg/kg, about 20 mg/kg, or about 25 mg/kg.

4. The method of claim 1, wherein said method comprises administering said compound to said patient as a regimen.

5. The method of claim 1, wherein said method comprises administering said compound to said patient orally or by intraperitoneal methods.

6. The method of claim 4, wherein said method comprises administering said compound to said patient daily.

7. The method of claim 6, wherein said method comprises administering said compound to said patient once a day (QD), twice a day (BID), or three times a day (TID).

8. The method of claim 1, wherein said method of treating cancer inhibits metastasis of said cancer in said patient.

9. The method of claim 1, wherein said method of treating cancer prolongs the time to disease progression of said cancer in said patient.

10. The method of claim 1, wherein said method of treating cancer prolongs the survival of said patient.

11. The method of claim 1, wherein said method of treating cancer increases progression-free survival of said patient.

12. The method of claim 1, wherein said method of treating cancer reduces tumor or tumor burden in said patient.

13. The method of claim 1, wherein dual specificity phosphatase 6 (DUSP6) expression reduces to 48% compared to housekeeping genes.

14. The method of claim 1, wherein dual specificity phosphatase 6 (DUSP6) expression levels can be used as a biomarker.

15. The method of claim 1, wherein phosphorylated extracellular signal-regulated kinase (pERK) expression reduces to 95% compared to housekeeping genes.

16. The method of claim 1, wherein said cancer is non-small cell lung cancer, esophageal cancer, stomach cancer, or brain tumor.

17. A method of decreasing tumor volume in a patient having non-small cell lung cancer, esophageal cancer, stomach cancer or brain tumor, wherein said patient has failed an EGFR TK inhibitor therapy, said method comprising administering to said patient a therapeutically effective amount of a compound having the structure of Formula (Ia), or a pharmaceutically acceptable salt or solvate thereof:

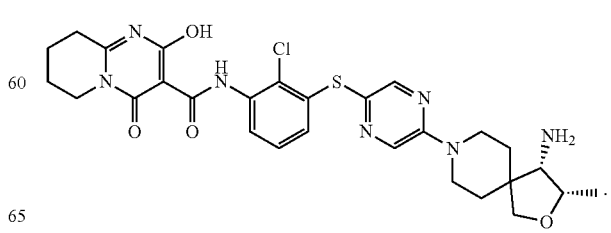

18. The method of claim 17, wherein said tumor volume is decreased by about 10%, about 20%, about 30%, about 40% or about 50%.

19. The method of claim 17, wherein said tumor volume is decreased by at least about 10%.

20. The method of claim 17, wherein said compound, or a pharmaceutically acceptable salt thereof is administered to said patient in need at about 5 mg/kg, about 10 mg/kg, about 15 mg/kg, about 20 mg/kg, or about 25 mg/kg.

21. The method of claim 17, wherein said method comprises administering said compound to said patient as a regimen.

22. The method of claim 17, wherein said method comprises administering said compound to said patient orally or by intraperitoneal methods.

23. The method of claim 17, wherein said method comprises administering said compound to said patient daily.

24. The method of claim 23, wherein said method comprises administering said compound to said patient once a day (QD), twice a day (BID), or three times a day (TID).

25. The method of claim 21, wherein said method comprises administering said compound to said patient for 7 days, 14 days or 21 days.

26. The method of claim 17, wherein said patient is undergoing treatment for non-small cell lung cancer.

* * * * *